United States Patent [19]

Drewlow et al.

[11] Patent Number: 5,684,225
[45] Date of Patent: *Nov. 4, 1997

[54] DOUBLE-FLOWERING NEW GUINEA IMPATIENS

[75] Inventors: Lyndon W. Drewlow; Edward P. Mikkelsen, both of Ashtabula, Ohio; James C. Mikkelsen, Fripp Island, S.C.

[73] Assignee: Mikkelsens, Inc., Ashtabula, Ohio

[*] Notice: The term of this patent shall not extend beyond the expiration date of Pat. No. Plant 8,018, Plant 8,893, Plant 8,905, Plant 8,906, Plant 8,916 and Plant 8,917.

[21] Appl. No.: 370,529

[22] Filed: Jan. 9, 1995

Related U.S. Application Data

[63] Continuation of Ser. No. 910,905, Jul. 10, 1992, Pat. No. 5,399,798.

[51] Int. Cl.$^6$ .................. A01H 5/00; A01H 5/10
[52] U.S. Cl. .................. 800/200; 800/255; Plt./87.6
[58] Field of Search .................. 800/200, 250, 800/255, DIG. 67; Plt./87.6

[56] References Cited

U.S. PATENT DOCUMENTS

| P.P. 3,918 | 6/1976 | Hope et al. | Plt./68 |
|---|---|---|---|
| P.P. 3,919 | 6/1976 | Hope et al. | Plt./68 |
| P.P. 3,920 | 6/1976 | Hope et al. | Plt./68 |
| P.P. 3,921 | 6/1976 | Hope et al. | Plt./68 |
| P.P. 3,922 | 6/1976 | Hope et al. | Plt./68 |
| P.P. 3,930 | 6/1976 | Hope et al. | Plt./87.6 |
| P.P. 6,298 | 9/1988 | Drewlow et al. | Plt./68 |
| P.P. 7,130 | 1/1990 | Simchock | Plt./68 |
| P.P. 7,690 | 10/1991 | Cole | Plt./68 |
| P.P. 8,220 | 5/1993 | Simchock | Plt./87.6 |
| P.P. 8,893 | 9/1994 | Drewlow | Plt./87.6 |
| P.P. 8,905 | 9/1994 | Drewlow | Plt./87.6 |
| P.P. 8,906 | 9/1994 | Drewlow | Plt./87.6 |
| P.P. 8,907 | 9/1994 | Drewlow | Plt./87.6 |
| P.P. 8,916 | 9/1994 | Drewlow | Plt./87.6 |
| P.P. 8,917 | 9/1994 | Drewlow | Plt./87.6 |
| 5,399,798 | 3/1995 | Drewlow et al. | 800/200 |

FOREIGN PATENT DOCUMENTS 548971  5/1993  European Pat. Off. ......... A01H 5/02

OTHER PUBLICATIONS

Arisumi, T., *J. Amer. Soc. Hort. Sci.*, 98:599–601 (1973).
Ball Seed Company Catalog 1992–93, p.51.
Vaughan's Seed Company Catalog 1992, p.36.
Simmonds, N. W., "Principles of Crop Improvement", Longman, London, Chapter 5, pp. 123–204, Breeding Plans, (1979).
Allard, R. W., "Breeding Methods of Self Pollinated Crops", *Principles of Plant Breeding*, John Wiley Sons, New York, Section 3, pp. 109–165 (1960); Breeding Methods with Cross Pollinated Crops, Section 5, pp. 252–322.
Kuckuck, Hermann, "Zierpflanzen", *Gartenbauliche Pflanzenzüchtung*, Verlag Paul Parey, Berlin, Chapter 3, pp. 138–185 (1979).
Wicki–Freidl, P., "Bei Fleissigen Lieschen Sind Auch die Züchter Fleissig", *Deutscher Gartenbau*, vol. 45, No. 4, pp. 206–209 (1991).

Armstrong, R. J., "An Impatiens Circus, the Longwood New Guinea Hybrid Impatiens", *American Horticulture*, vol. 53, No. 1, pp. 14–18 (1974).
Arisumi, T., "Phenotypic Analysis of Progenies of Artificial & Natural Amphiploid Cultivars of New Guinea & Indonesian Species of Impatiens L", *Journal American Horticultural Society*, vol. 100, No. 4, pp. 381–383, (1975).
Stephens, L. C., et al., "Micropropagation of Impatiens spp", *Biotechnology in Agriculture and Forestry*, vol. 20, High-Tech in Micropropagation IV, pp. 160–172, Ch. XII (1992).
Hay, R. & Becket, K. A., "Reader's Digest Encyclopaedia of Garden Plants and Flowers", Reader's Digest Ass. Ltd., London (1988).
Benjamin, Joan Marie (Aug. 1990) Master's Thesis: Public Horticulture Administration at the University of Delaware, "The History and Development of New Guinea Impatiens".
Han, Kyungchulan and Stephens, Loren C., *Scientia Horticulturae*, "Growth Regulators Affect In Vitro Propagation of Two Interspecific Impatiens Hybrids", 32:307–313 (1987).
Grey–Wilson, C., *Kew Bulletin*, "Impatiens in Papuasia: Studies in Balsaminaceae: I", 34:661–668 (1979).
Pasutti, David, W., and Weigle, Jack, L., *Can. J. Bot.*, "Pollen Fertility in Java x New Guinea Impatiens Interspecific Hybrids", 58:384–387 (1980).
Weigle, J.L., and Pasutti, D.W., "Approaches to Transfer of Characteristics Between Ploidy Levels in New Guinea Impatiens", *Acta Horticulturae*, 63:109–112 (1976).
Stephens, L.C., et al., *HortScience*, "In Vitro Propagation of Java, New Guinea and Java x New Guinea Impatiens", 20(3):362–363 (1985).
Arisumi, T., *HortScience*, "Chromosome Numbers and Breeding Behavior of Hybrids Among Celebes, Java, and New Guinea Species of Impatiens L", 9(5):478–479 (1974).
Arisumi, T., *The Journal of Heredity*, "Chromosome Numbers and Interspecific Hybrids Among New Guinea Impatiens Species", 64:77–79 (1973).
Beck, Allan, R., et al., *Can.J.Bot.*, "Breeding Behavior and Chromosome Numbers Among New Guinea and Java Impatiens Species, Cultivated Varieties, and Their Interspecific Hybrids", 52:923–925 (1974).
Arisumi, T., *J. Am. Hort. Sci.*, 112(6): 1026–1031 (1987).

*Primary Examiner*—Douglas W. Robinson
*Assistant Examiner*—Melissa L. Kimball
*Attorney, Agent, or Firm*—Foley & Lardner

[57] ABSTRACT

New, distinct and stable cultivars of double-flowering New Guinea Impatiens (NGI) are disclosed. Double-flowering NGI produce one or more flowers with at least seven full or partial petals per flower. Double-flowering NGI cultivars are disclosed in which substantially all the flowers produce at least 7 full or partial petals per flower. The double-type flower characteristic has been successfully bred into all single-type (5 petals per flower) or semi-double-type (6 petals per flower) NGI cultivars thus far tested. The double-type flower characteristic has been combined with many desirable NGI traits including different flower colors, leaf colors, leaf variegation, and growth habits. Methods for the reliable breeding of the double-type characteristic into diverse single-type or semi-double-type NGI genetic backgrounds, as well as methods for increasing the degree of doubleness per flower or plant, are disclosed.

8 Claims, 25 Drawing Sheets

DOUBLE-FLOWERING NEW GUINEA IMPATIENS

This is a continuation of application Ser. No. 07/910,905 filed Jul. 10, 1992, now U.S. Pat. No. 5,399,798.

FIELD OF THE INVENTION

The present invention relates to new, distinct and stable cultivars of double-flowering New Guinea Impatiens (NGI). Double-flowering NGI cultivars produce an inflorescence containing one or more flowers having at least seven full or partial petals per flower. NGI cultivars normally produce flowers having 5 petals (single-type) or rarely 6 petals (semi-double-type).

The present invention relates to double-flowering NGI cultivars which produce an inflorescence wherein substantially all the flowers have at least 7 full or partial petals per flower. The double-type flower characteristic can be bred into diverse single-type or semi-double-type NGI genetic backgrounds. The double-type flower characteristic can be combined with many other known and desirable NGI characteristics including different flower colors, flower forms, leaf colorations, growth habits, etc.

The present invention also relates to methods for the breeding of the double-type characteristic into single-type or semi-double-type NGI cultivars. The present invention also relates to methods for increasing the degree of doubleness per flower or plant.

BACKGROUND OF THE INVENTION

Impatiens has become an increasingly important ornamental crop. In 1970, in order to increase the germplasm pool for this crop, the U.S. Department of Agriculture introduced 23 Impatiens from New Guinea, 1 from Celebes and 1 from Java. H. F. Winters, *Am. Hotic.*, 52, 923 (1973). New Guinea Impatiens (NGI) encompasses a group of interbreeding species that include I. schlecteri Warb., I. herzogii K. Schum, *I. linearifolia* Warb., *I. mooreana* Schltr., *I. hawkeri* Bull, and other species of the same geographic origin which are interfertile. NGI are diverse phenotypically, producing large flowers with colors ranging from white to various shades of lavender, red, pink and orange. The leaves are of various shapes and sizes, with and without variegations. C. Grey-Wilson, *Kew Bulletin*, 34, 661 (1979). Although diverse phenotypically, members of NGI are interfertile and generally have a 2n chromosome number of 32. T. Arisumi, *J. Hered.*, 64:77 (1973).

Java and Celebes Impatiens are known as *I. platypetala* Lindl. and *I. platylpetala aurantiaca* Steen, respectively. K. Hah et al., *Scientia Horticulturae*, 32, 307 (1987). The introduced species from New Guinea, Celebes and Java generally have been found to cross readily among themselves, even though their somatic chromosome numbers vary. D. W. Pasutti et al., *Can. J. Bot.*, 58, 384, (1980); J. L. Weigle et al., *Acta Horticulureae*, 63,109 (1976); A. R. Beck et al., *Can. J. Bot.*, 52, 923 (1974); T. Arisumi, *HortScience*, 95:478 (1974).

The expected merger of New Guinea, Celebes and Java into Impatiens of African origin, such as the Sultana Impatiens (*I. wallerana*), has not occurred because of incompatibility barriers. A. R. Beck et al., *Can. J. Bot.*, 52, 923 (1974). Despite incompatibility with Impatiens of African origin, NGI cultivars have become popular in their own right as ornamentals. The NGI group produces a wider array of leaf variegation and larger flowers with more brilliant colors than the nonvariegated and seed-propagated species of African origin.

L. C. Stephens, *HortScience*, 20, 362 (1985), which is incorporated herein by reference, teaches methods for the in vitro propagation of NGI that offers the advantages of a continuous source of vegetative shoots and the production of more shoots per unit of time than traditional vegetative propagation methods. K. Han et al., *Scientia Horticulturae*, 32, 307 (1987), which is incorporated herein by reference, teach methods for the in vitro propagation of Celebes, Java, and NGI and interspecific hybrids of Celebes or Java and NGI.

Commercial bedding Impatiens of African origin, such as *I. wallerana*, are known which produce more than 5 petals per flower (Plant Patent No. 7,690). NGI cultivars, however, typically produce flowers having five petals per flower. The cultivar "Aurora", described in Plant Patent No. 6298, has been observed to occasionally, but not consistently, produce flowers having a sixth small partial petal per flower. The breeding of NGI cultivars which produce one or more flowers having at least seven petals per flower would offer a choice of unique flower form to compliment the presently available and popular NGI cultivars having five petals per flower.

SUMMARY OF THE INVENTION

An object of the present invention is to provide New Guinea Impatiens cultivars having one or more double-type flowers with at least seven full or partial petals per flower.

An object of the present invention is to provide New Guinea Impatiens cultivars which produce an inflorescence wherein substantially all the flowers are double-type with at least 7 full or partial petals per flower.

Another object of the present invention is to provide methods for the breeding of the double-type flower characteristic into diverse single-type or semi-double-type New Guinea Impatiens genetic backgrounds.

An object of the invention is to provide a method for breeding double-flowering New Guinea Impatiens plants that produce one or more flowers with at least 7 full or partial petals per flower comprising the steps of (a) crossing a first semi-double-type plant, either as the male or female parent to (i) a second semi-double-type plant; (ii) a double-type plant; (iii) a single-type plant having doubleness in its genetic background; (b) selecting F1 progeny that are single-type, semi-double-type or double-type; (c) crossing said F1 progeny that are single-type, semi-double-type or double-type to (i) a second double-type plant; (ii) a third semi-double-type plant; (iii) a second single-type plant having doubleness in its genetic background; or (iv) a second single-type plant having no known doubleness in its genetic background and (d) selecting double-flowering progeny. The second single-type and double-type plants, or first, second and third semi-double-type plants are the same or different cultivars.

Another object of the invention is to provide a method for the breeding of double-flowering New Guinea Impatiens plants that produce one or more flowers with at least 7 full or partial petals per flower comprising the steps of (a) crossing a first double-type plant, either as the male or female parent to (i) a semi-double-type plant; (ii) a second double-type plant; (iii) a single-type plant having doubleness in its genetic background; or (iv) a single-type plant with no known doubleness in its genetic background; (b) selecting F1 progeny that are single-type, semi-double-type or double-type; (c) crossing said F1 progeny that are single-type, semi-double-type or double-type to (i) a third double-type plant; (ii) a second semi-double-type plant; (iii) a second single-type plant having doubleness in its genetic background; or (iv) a second single-type plant with no known doubleness in its genetic background; and (d) selecting double-flowering progeny. The first, second and third double-type plants, or first and second single-type or semi-double-type plants are the same or different cultivars.

An additional object of the present invention is to provide methods for increasing the degree of doubleness per flower or plant in selected New Guinea Impatiens cultivars.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION

Figure 1:
FIG. 1. New Guinea Impatiens cultivar 89-717-1 which produces single-type flowers having five petals per flower.

As used herein, "single", "single-type", or "singleness" are each defined as the typical New Guinea Impatiens (NGI) plant which produces flowers having five petals per flower or the typical NGI flower which has five petals.

As used herein, "semi-double", "semi-double-type", or "semi-doubleness" are each defined as a NGI plant which produces one or more flowers having a sixth full or partial petal per flower or a NGI flower which has a sixth full or partial petal.

As used herein, "double", "double-type", "double-flowering", or "doubleness" are each defined as a NGI plant which produces one or more flowers having at least 7 full or partial petals per flower or a NGI flower which has at least 7 full or partial petals. Double-flowering NGI cultivars are genetically stable. Double-flowering cultivars can be stably reproduced by means of asexual propagation. The characteristic of doubleness can be predictably bred into diverse single-type and semi-double-type NGI genetic backgrounds.

As used herein, the "degree of doubleness per flower" is defined as a measure of the number of extra full or partial petals per flower produced beyond the number five normally found on NGI cultivars. The greater the degree of doubleness per flower, the greater the number of full or partial petals produced per flower.

As used herein, the "degree of doubleness per plant" is defined as a measure of the number of flowers per plant which have at least 7 petals per flower. The greater the degree of doubleness per plant, the higher is the percentage of total flowers produced by the plant which have at least 7 full or partial petals per flower.

As already noted, double-type NGI cultivars are genetically stable, as evidenced by the stability of the trait through both asexual propagation and sexual crosses. Depending upon the cultivar, however, the degree of doubleness per flower or plant may be adversely affected by environmental stress factors, without any variance in the genotype of the plant. Environmental stress factors which adversely affect flowering of NGI plants generally, such as high temperatures, low soil fertility or water stress, may adversely affect the degree of doubleness per flower or plant. Most notably, the degree of doubleness per flower or plant may decline with increasing temperatures, especially in the range of 30° C. and above. NGI cultivars have been successfully selected, as reported herein, in which the degree of doubleness per flower or plant is not greatly affected by high temperature. Among cultivars in which the degree of doubleness per flower or plant is adversely affected by temperature, however, the degree of doubleness is restored with removal of the environmental stress factor(s).

NGI, Java and Celebes are crossed using known and conventional methods. Plants to be crossed are usually grown in 25 cm pots containing a porous peat styrofoam artificial soil. The plants are grown at 65°–68° F. night temperature and 3000 to 4000 foot candles of light. They are watered with a solution containing 250 parts per million (ppm) nitrogen, 75 ppm potassium and 250 ppm phosphorous. Trace elements are added to the soil mix. Crosses can be made throughout the year. The highest success rate, however, is observed during cooler winter months. The flower to be used as the female parent is not emasculated. Emasculation is not necessary because the stigmatic surface of the pistil is not receptive when the anther hood that covers the pistil is shedding pollen. The anther hood is removed if it dries around the pistil before pollination. Depending upon the environmental conditions, the stigmatic surface is receptive for 1 to 2 days following the loss of the anther hood. Under warmer temperatures, particularly above 75° F., the period of pollen receptivity decreases rapidly after loss of the anther hood.

Flowers to be used as the source of male parent pollen are picked from the plant and used to pollinate from 3 to 5 flowers of the same cross combination. Pollen is shed from the center of the anther hood and this is the area which is applied to the stigmatic surface. In this fashion, an abundance of pollen is delivered to the stigmatic surface. A tag is placed on each pollinated flower on which is recorded the date of pollination and the identity of male and female parents.

The seed pods from successful pollinations are placed in glasine bags approximately three weeks after pollination. The glasine bags catch seeds released upon explosion of the seed pods at ripening. Ripening of the seed pods occurs 4 to 5 weeks after pollination, depending upon the environmental conditions. Cool and cloudy weather increases the time required for ripening of the seed pods. The collected seeds are cleaned by hand. The seeds are separated from the pod chaff and stored in glasine bags. The seeds must be planted within approximately 90 days of seed pod ripening because seed viability decreases rapidly.

Flowers from semi-double-type or double-type cultivars maintain functional male and female organs. The incorporation of the double-type trait into other NGI cultivars, therefore, has been possible. Doubleness has been incorporated into cultivars with many different flower colors, including cultivars with bicolor flowers (Tables IV, V, IX and XI). Doubleness has been incorporated into cultivars with solid green foliage, green and yellow variegated foliage, dark green foliage, dark green and yellow variegated foliage, dark purplish leaves, dark purplish and cream variegated foliage, more than one flower per leaf axil, semi-dwarf habit, tall stature, upright growth habit, mounded growth habit, etc. Doubleness, therefore, has been successfully incorporated into many different NGI genetic backgrounds and combined with a wide range of known and desirable NGI characteristics.

Plants carrying genes controlling the double-flowering phenotype can be selected from any NGI population by means of identifying a plant having one or more flowers with 6 petals per flower. The NGI population may be a single species, or a population of plants composed of two or more species within the NGI group. The frequency with which plants having one or more flowers with 6 petals per flower occur within a NGI population comprised of interbreeding species was determined. The NGI population of interbreeding species included *I. schlecteri* Warb., *I mooreana* Schltr., *I herzogii* K. Schum., *I linearifolia* Warb. and *I hawkeri* Bull. A total of 12 plants having one or more flowers with 6 petals per flower was found among 8,000 plants screened in the breeding population. Any one of the plants identified in the NGI population that has one or more semi-double-type flowers can be used as a source of double-type genes in a breeding program having the goal of producing new double-flowering NGI varieties.

A plant with one or more semi-double-type flowers is identified in a NGI population and used to breed new double-flowering NGI varieties by selfing over a number of generations with periodic outcrossing to circumvent inbreeding depression and to introduce desirable traits into the breeding program. The doubleness trait can be fixed in the breeding population by means of recurrent selection.

Alternatively, the selected plant with one or more flowers with 6 petals per flower can be crossed with another independently identified semi-double-type or double-type selection. Progeny from this cross having desirable characteristics can then be selfed to intensify expression of the doubleness trait, with periodic outcrossing to circumvent inbreeding depression and to introduce desirable characteristics into the breeding program.

It is expected that doubleness can be introduced into interspecific hybrids made between Celebes or Java and NGI double-type cultivars. A selected NGI double-type cultivar is crossed, using conventional methods, as either the male or female parent, to a selected Celebes or Java parent. The F1 progeny are then scored for the double-type phenotype.

It is expected that the degree of doubleness per flower or plant can be predictably increased in any NGI background using the methods herein described. Recurrent selection for progeny with an increased degree of doubleness has dramatically increased the degree of doubleness per flower or plant in diverse NGI genetic backgrounds. Intermating of superior genotypes which exhibit increased doubleness through repeated generations has resulted in the selection of cultivars with an increasing degree of doubleness per flower and plant. Periodic outcrossing is done during the breeding program in order to introduce desirable characteristics and to circumvent inbreeding depression.

It is expected that any selected double-type NGI cultivar can be produced commercially through asexual propagation.

All double-type cultivars thus far tested have been found to be stable through asexual propagation. Cuttings for asexual propagation can be taken at any time of the year and no special hormones or soil mixtures are used. It is also expected that NGI double-type cultivars can be produced as progeny from sexual crosses and sold as seed. Methods for the storage of NGI seed under low oxygen and moisture conditions for sale in commercial trade are well known.

The semi-double NGI variety 83-407-1 was first discovered amongst the seedling population resulting from the cross of Mikkelsen cultivar 82-581-1 to the cultivar 'Columbia', described in Plant Patent No. 5126. The selection 83-407-1 produces, under ideal growing conditions, light pink flowers with a single, underdeveloped, sixth petal. This selection did not grow vigorously and produced severely curled and crinkled leaves. Approximately 10–20% of the flowers produced by 83-407-1 had a sixth petal.

A breeding program was undertaken, using 83-407-1 as starting material, having the goal of selecting new and unique double-type NGI cultivars. This goal was accomplished by means of crossing 83-407-1 with selected NGI cultivars having characteristics of flower color, leaf variegation, etc. that were desired in the breeding program. Progeny were initially selected having one or more flowers with at least 6 full or partial petals per flower. Breeding of NGI cultivars having an increased degree of doubleness per flower or plant was accomplished by means of recurrent selection. Progeny with increased doubleness per flower or plant were selected and incorporated into the breeding program.

The breeding program also included outcrossing to increase genetic diversity, incorporate desirable NGI traits, and to circumvent inbreeding depression. The breeding program included backcrossing to 83-407-1, or other double-type parents selected during the breeding program. The breeding program also included sibcrossing among the progeny from crosses to double-types. The genealogies of double-type cultivars 90-132-2 and 90-139-14, produced using the breeding method described above, are shown in FIGS. 3 and 4, respectively. All crosses were made by conventional methods, described in detail hereinabove.

Figure 4A:
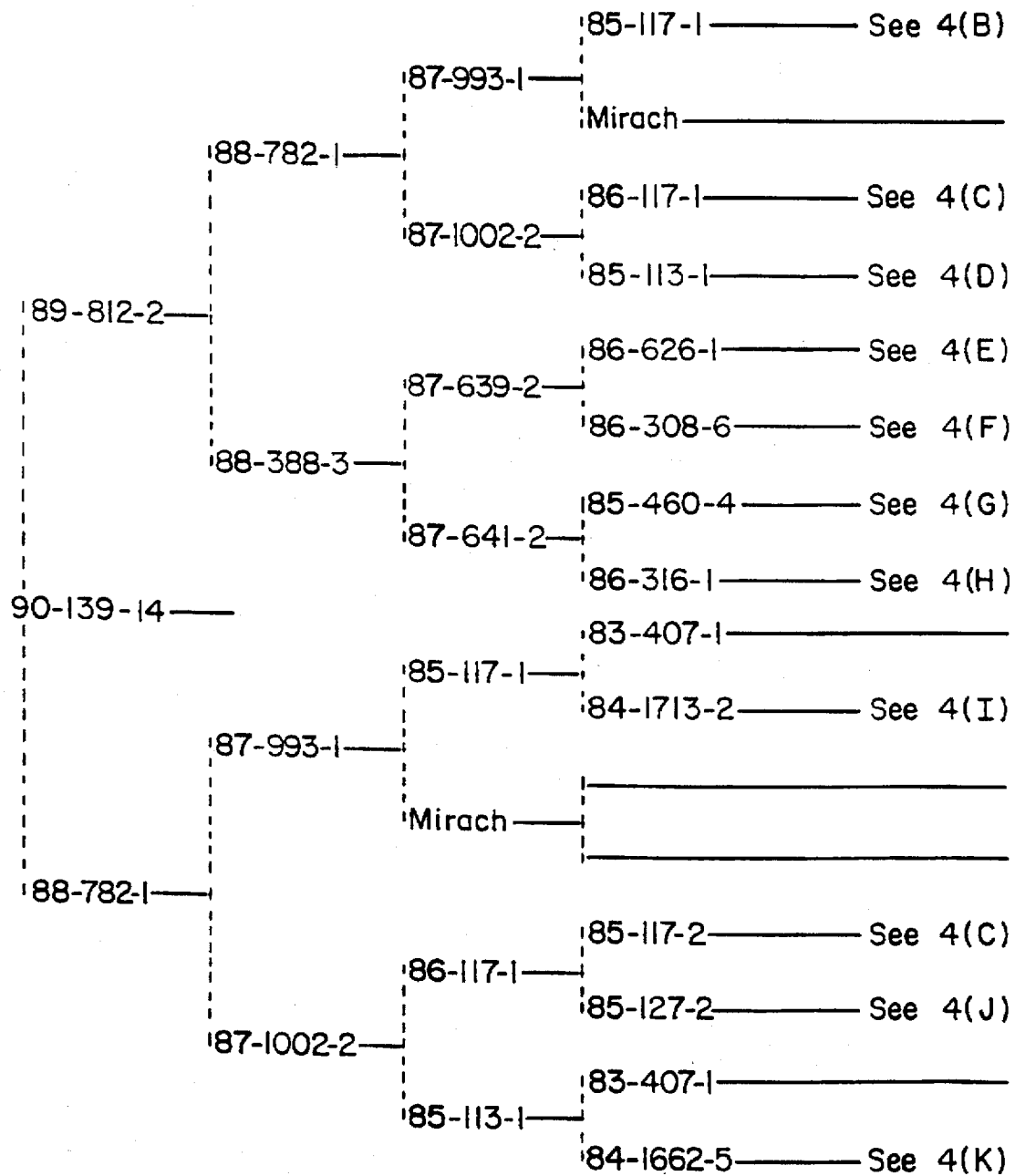
FIG. 4 (A–K). Genealogy of double-type cultivar 90-139-14. For each cross the male parent is shown above the female parent.
Figure 4B:
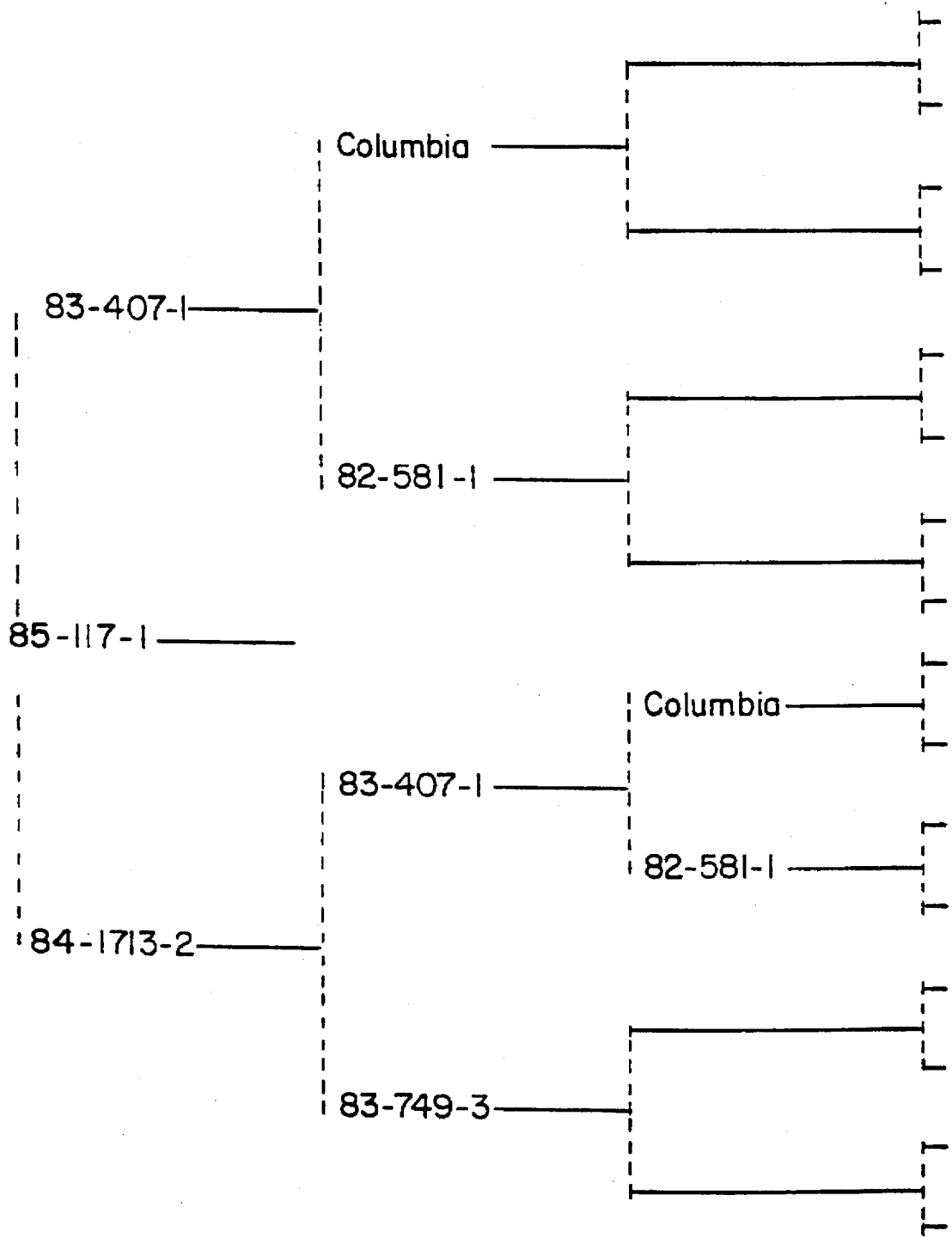
Figure 4C:
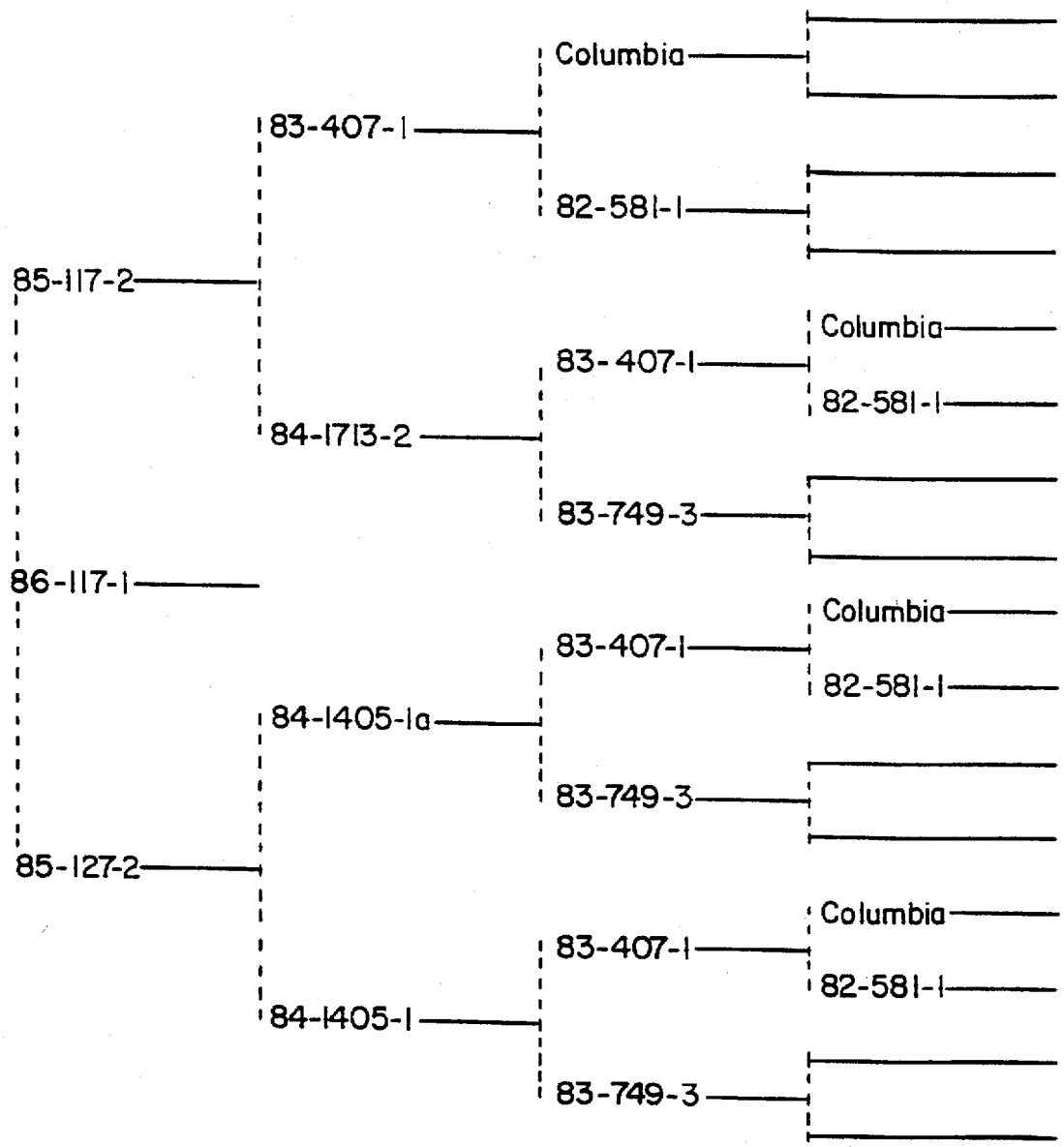
Figure 4:
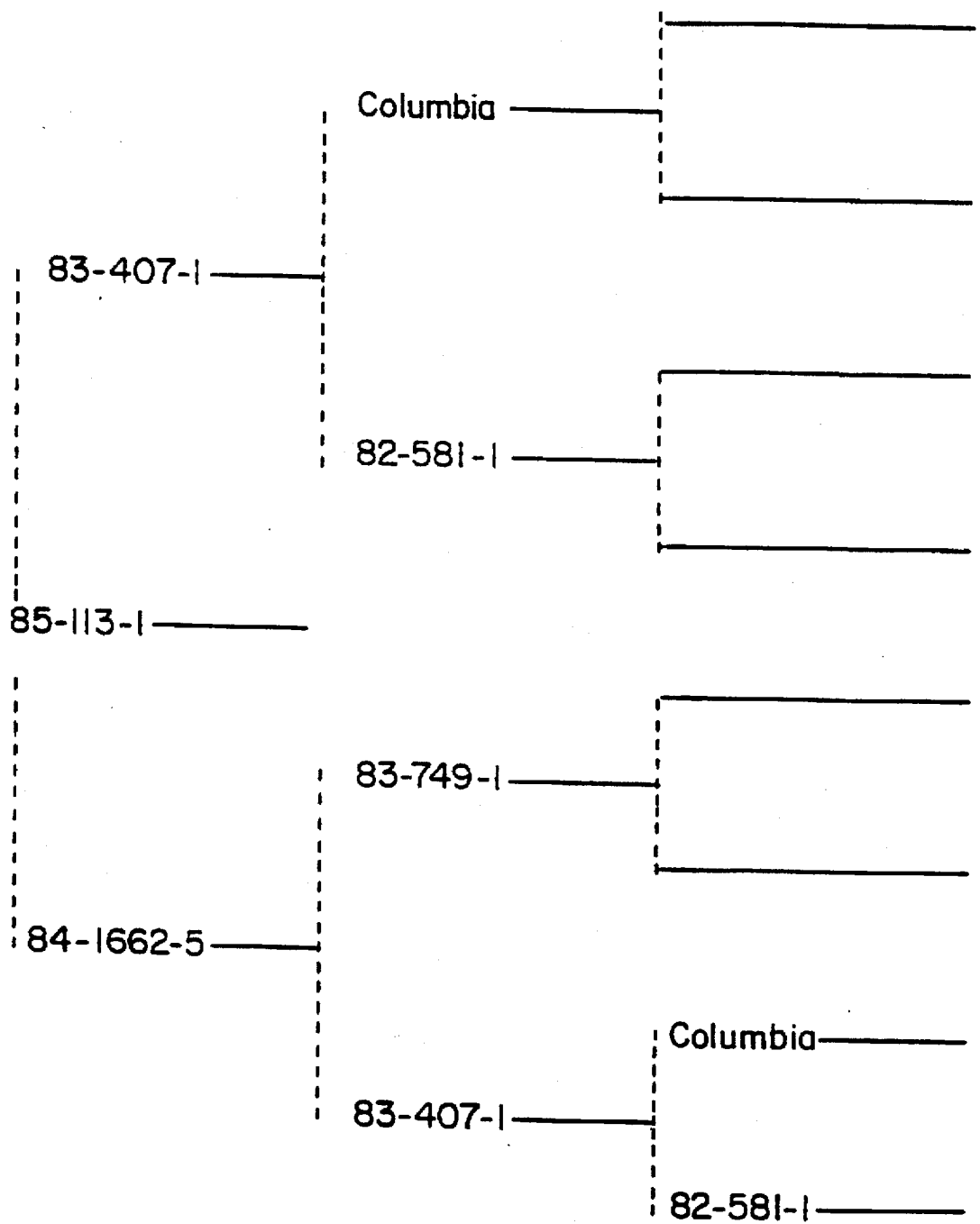
Figure 4E:
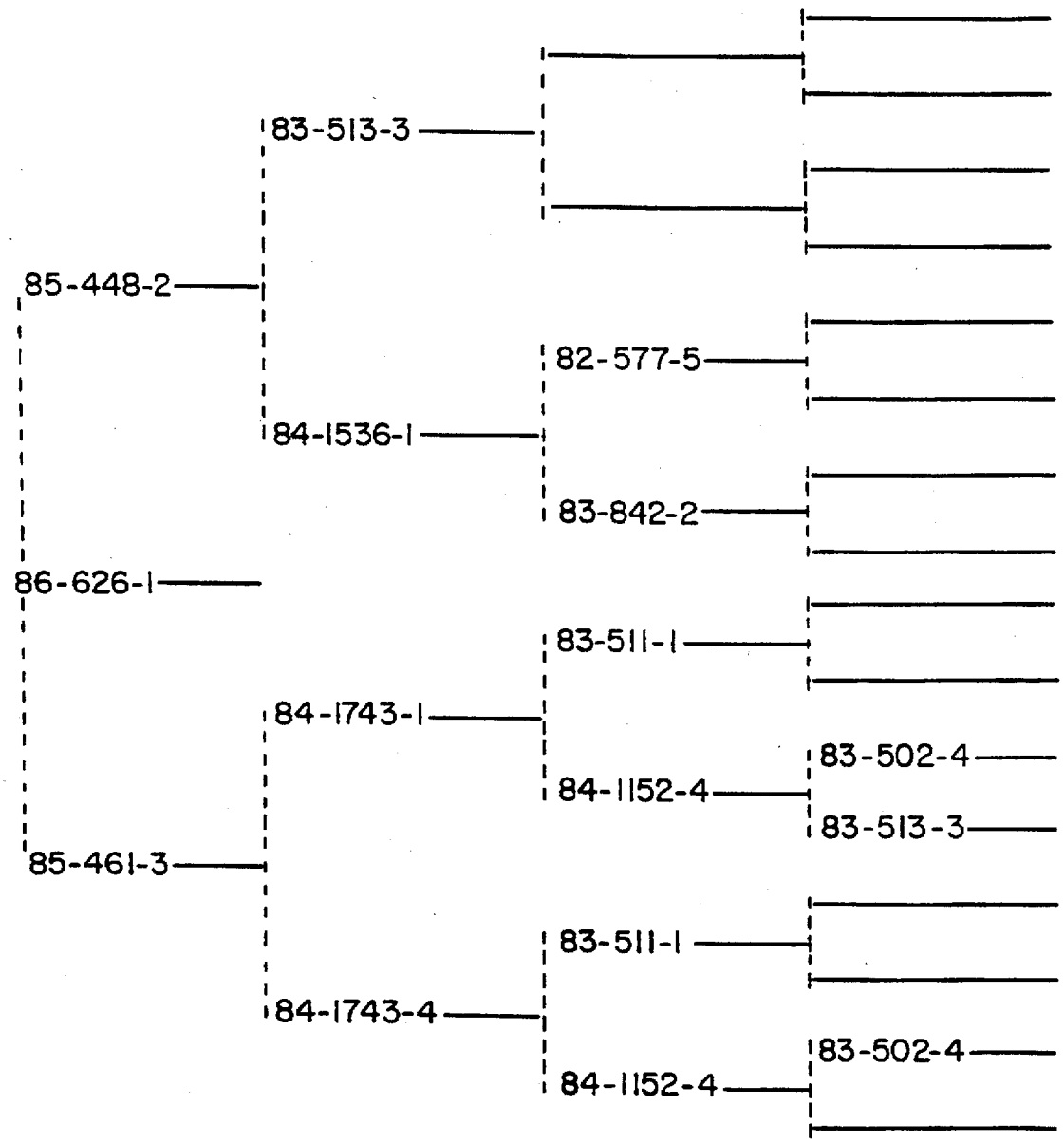
Figure 4:
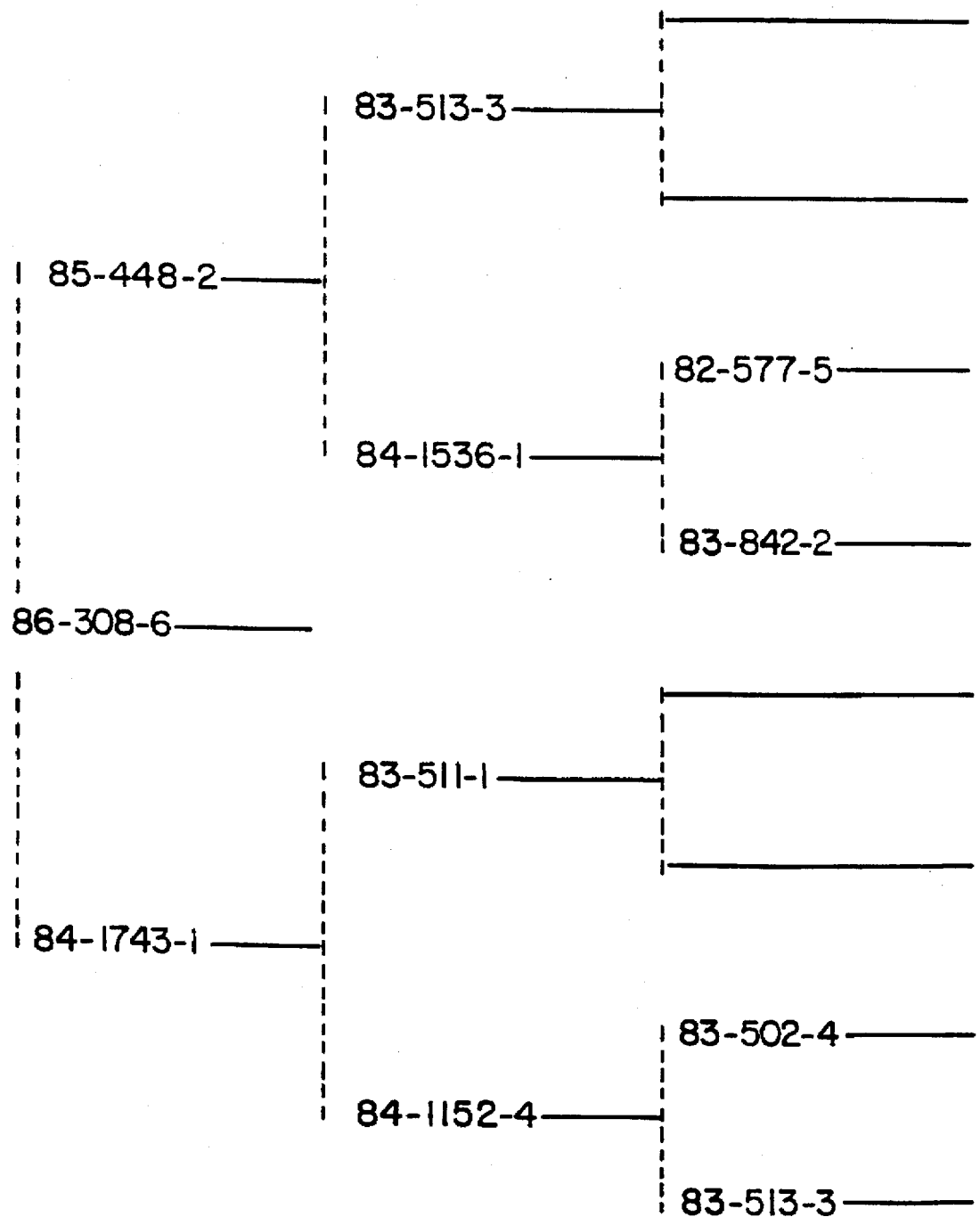
Figure 4G:
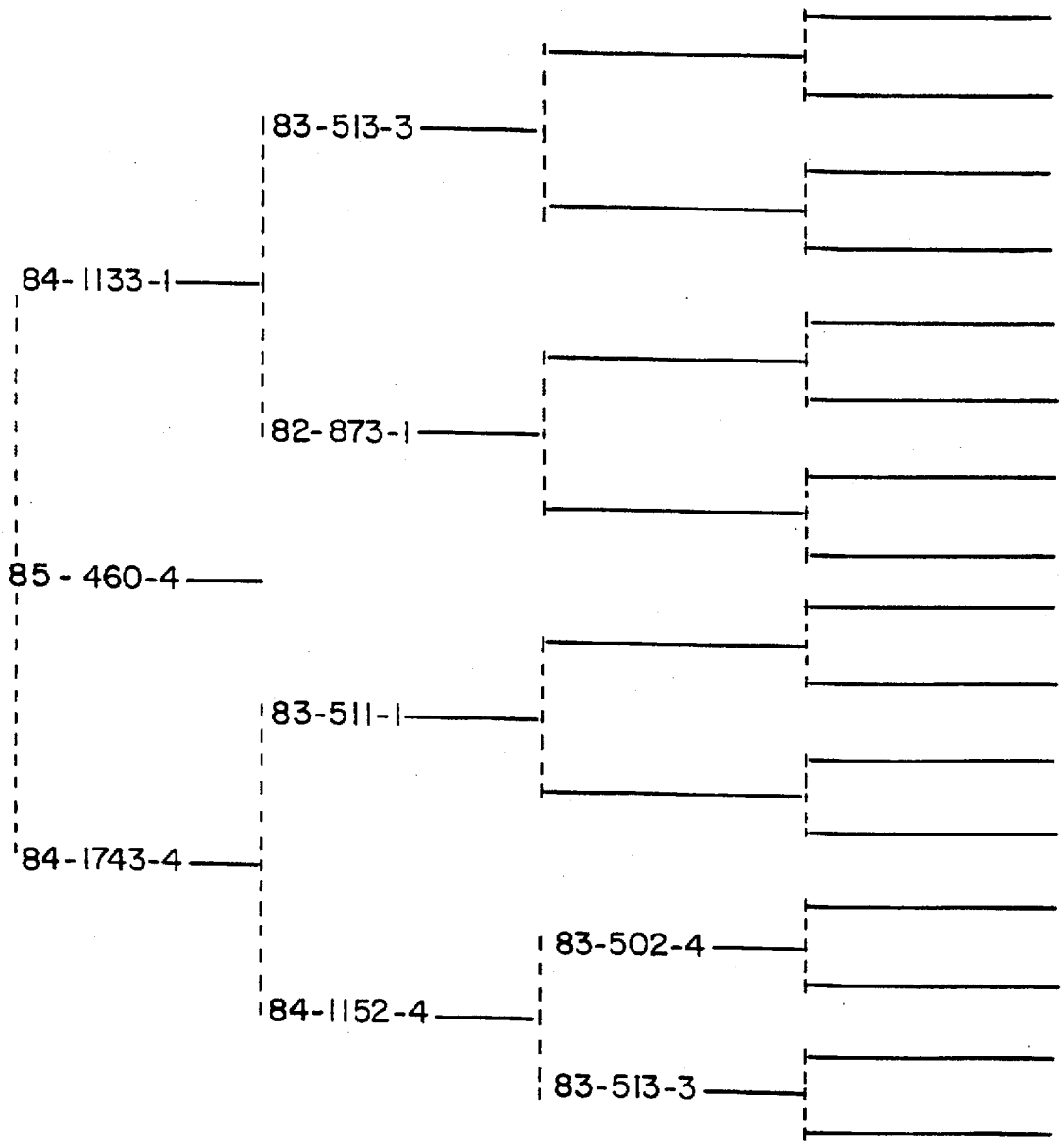
Figure 4H:
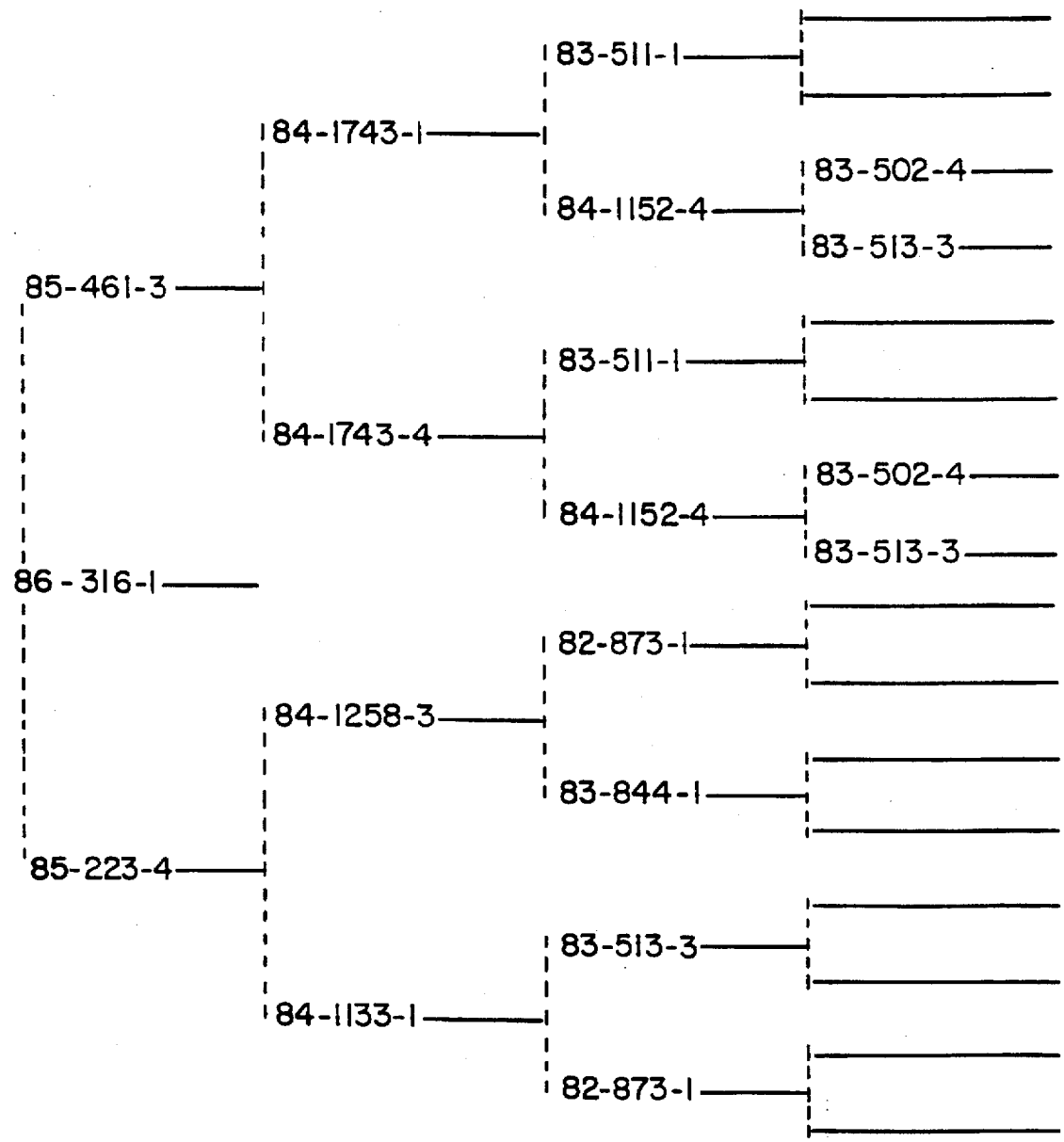
Figure 4:
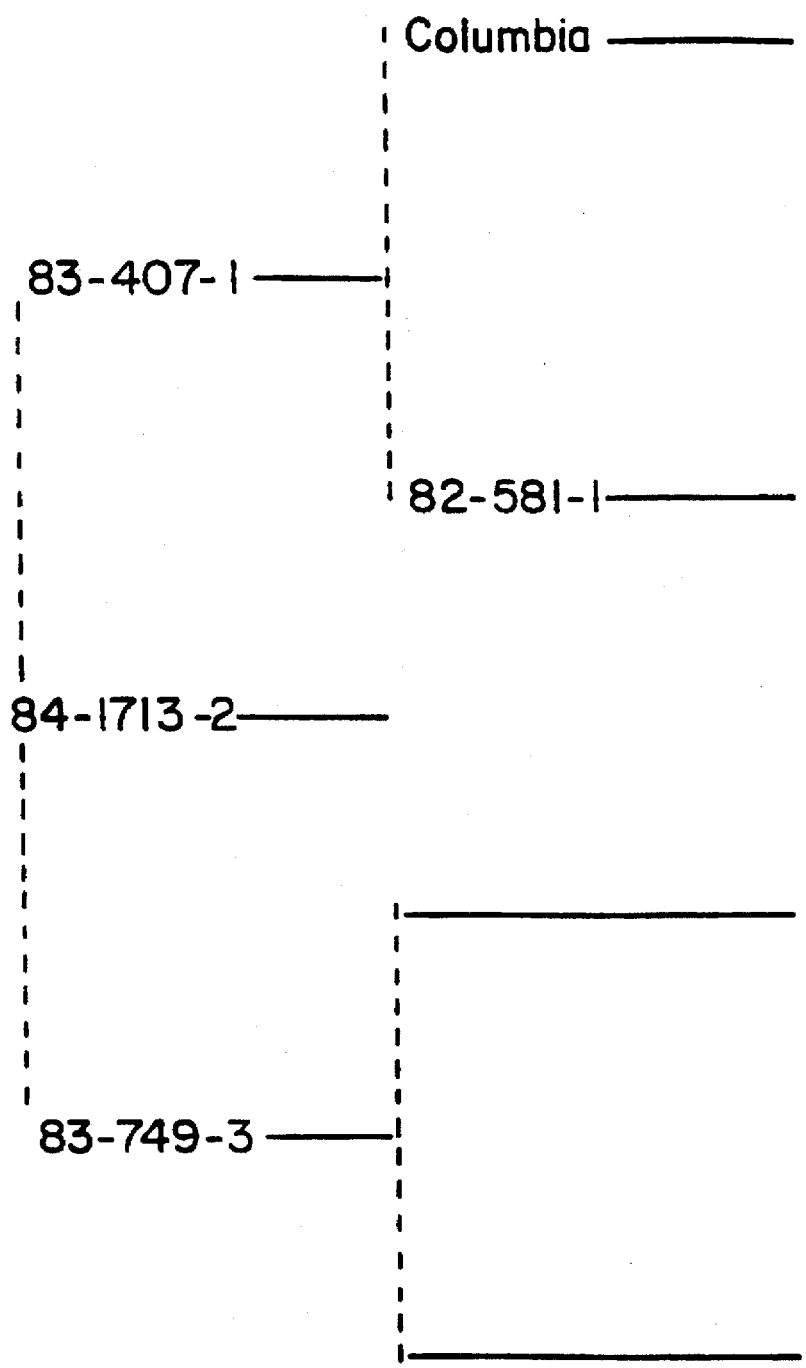
Figure 4J:
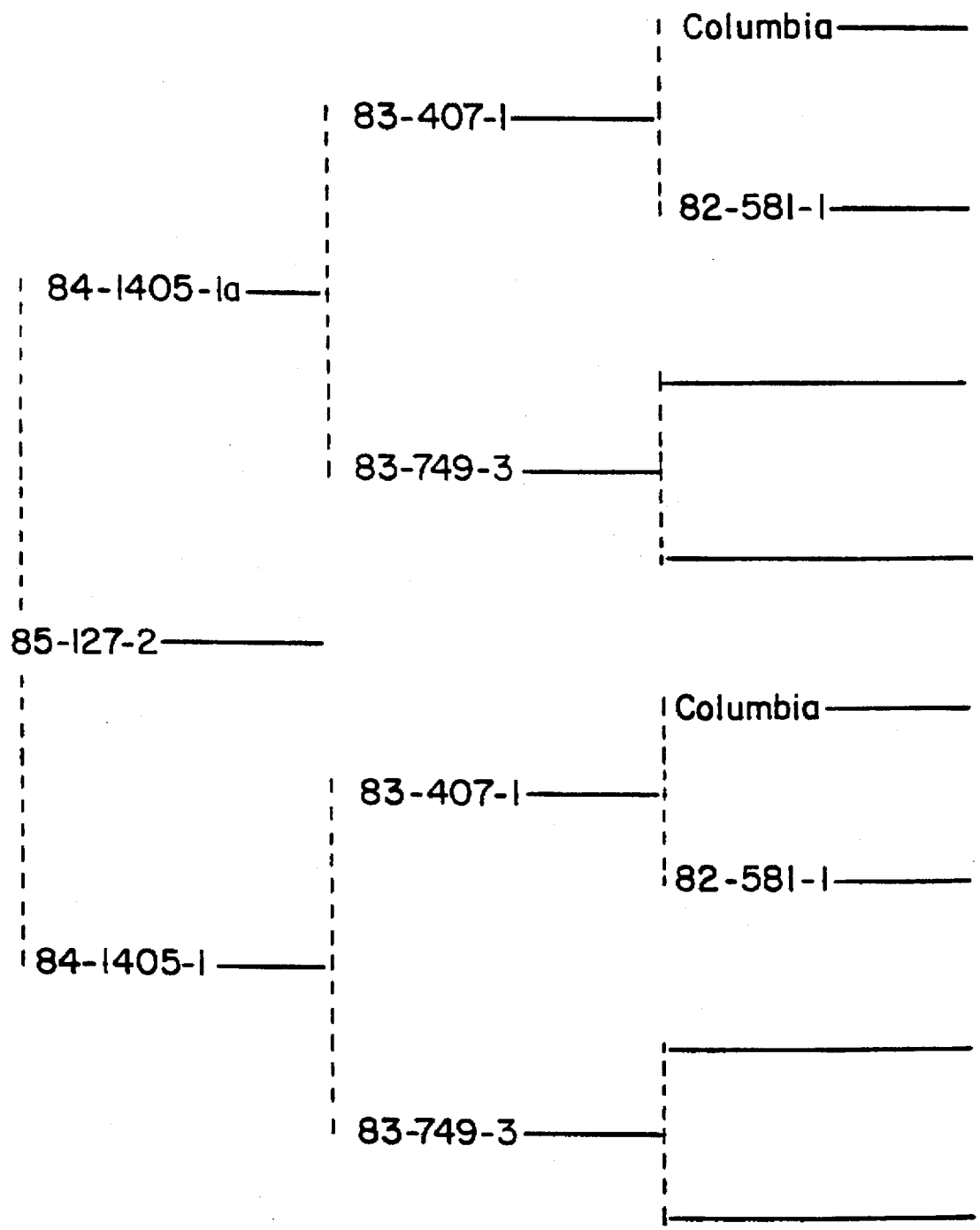
Figure 4K:
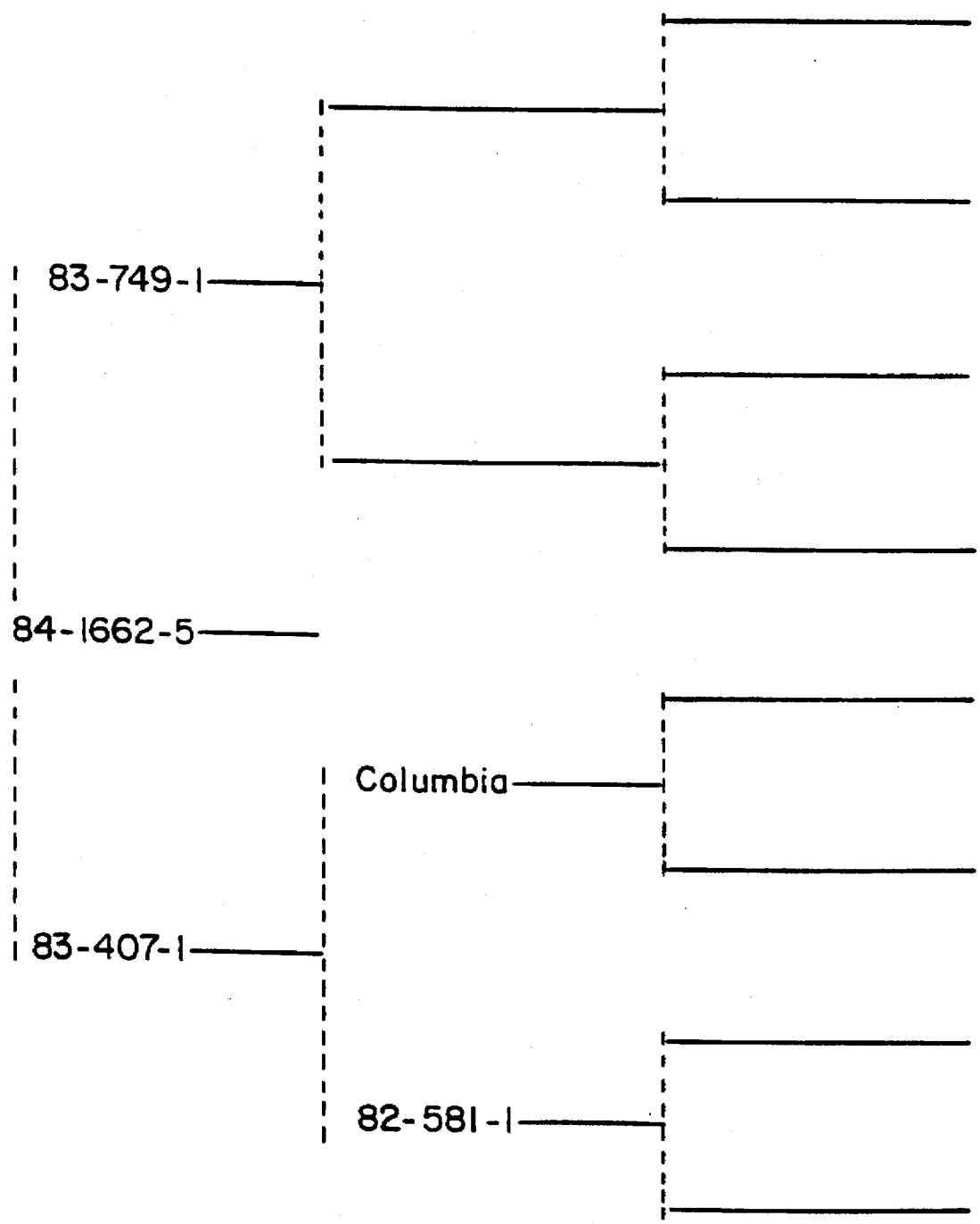

The selection 83-407-1 was crossed 26 times as the male parent with 26 different single-types and 23 of these crosses set seed. The selection 83-407-1 was crossed 14 times as the female parent with 14 different NGI single-type cultivars and 12 of these crosses set seed. The selection 83-407-1 was also selfed. No viable seeds were obtained from the selfing of 83-407-1. Single and semi-double-types were obtained from outcrossing 83-407-1. Semi-double-type progeny were selected which produced one or more flowers with a 6th full or partial petal (generation 1). Semi-double-type progeny from generation 1 were selfed. Seedlings produced from the selfing of the semi-double-type progeny were weak and of little breeding merit. Selected single and semi-double-type progeny were backcrossed to 83-407-1. Additionally, the selected single and semi-double-type progeny were crossed to cultivars with bicolored flowers and multiple flowers per node in an attempt to increase the genetic diversity into which doubleness was incorporated. Seeds obtained from these crosses were collected, sown and progeny selected (generation 2). Several selections were made which produced one or more flowers with 7 to 8 petals per flower. Selection 85-117-1, and its sibling 85-117-2, were parents in most of the best doubleness selections obtained in the next series of crosses. Selection 85-117-1 is found in the genealogy of 90-139-14 (FIG. 4). Selection 85-117-2 is found in the genealogies of both 90-132-2 (FIG. 3) and 90-139-14 (FIG. 4).

Crosses were made among the best selections for semi-doubleness and doubleness and the seeds produced were sown. The seedling population which resulted showed improvement for plant type and habit but very little progress in increasing the degree of doubleness per flower or plant (generation 3).

Once again, crosses were made among the best selections for semi-doubleness and doubleness. The original selection 83-407-1 was included in these crosses. Additionally, the cultivars 'Mirach' (Plant Patent No. 6309), 'Comet' (Plant Patent No. 5920) and 'Dawn' (Plant Patent No. 5775) were included in these crosses in order to introduce missing colors, dark-green leaves, improve plant habit and reduce leaf curling and crinkling among the double and semi-double selections. Progeny were selected that exhibited an increase in the degree of doubleness per flower or plant (generation 4). One selection obtained in generation 4, 87-1002-2, a product of the cross of 86-117-1 to 85-113-1, was a parent in most of the best doubleness selections obtained in the next series of crosses. The selection 87-1002-2 is found in the genealogies of both 90-132-2 (FIG. 3) and 90-139-14 (FIG. 4).

Crosses were made among the best double-type selections from generations 3 and 4. Progeny were selected that exhibited an increase in the degree of doubleness per flower or plant (generation 5). Among the progeny that were produced, selection 88-781-1, a product of the cross of 87-1002-2 to 87-995-4, and selection 88-782-1, a product of the cross of 87-993-1 to 87-1002-2, were parents in most of the best doubleness selections obtained in the next generation. Selection 88-781-1 is found in the genealogy of 90-132-2 (FIG. 3). Selection 88-782-1 is found in the genealogy of 90-139-14 (FIG. 4).

Crosses were made among the best selections from generations 3–5. In addition, some single-type selections were included in these crosses in order to introduce other colors and characteristics into the doubleness breeding program. Selection 88-781-1 was used four times as the male parent in these crosses. Selection 88-782-1 was used eight times as the male parent, and once as the female parent, in these crosses. No viable seeds were obtained when 88-782-1 was used as the female parent. Stable progeny were obtained in which substantially all the flowers in the inflorescence were double-type (generation 6).

Figure 2:
FIG. 2. New Guinea Impatiens cultivar 90-132-2 which produces double-type flowers in which substantially all flowers have 8–10 petals per flower. The photograph is of 90-132-2 flowering during the summer.
Figure 3A:
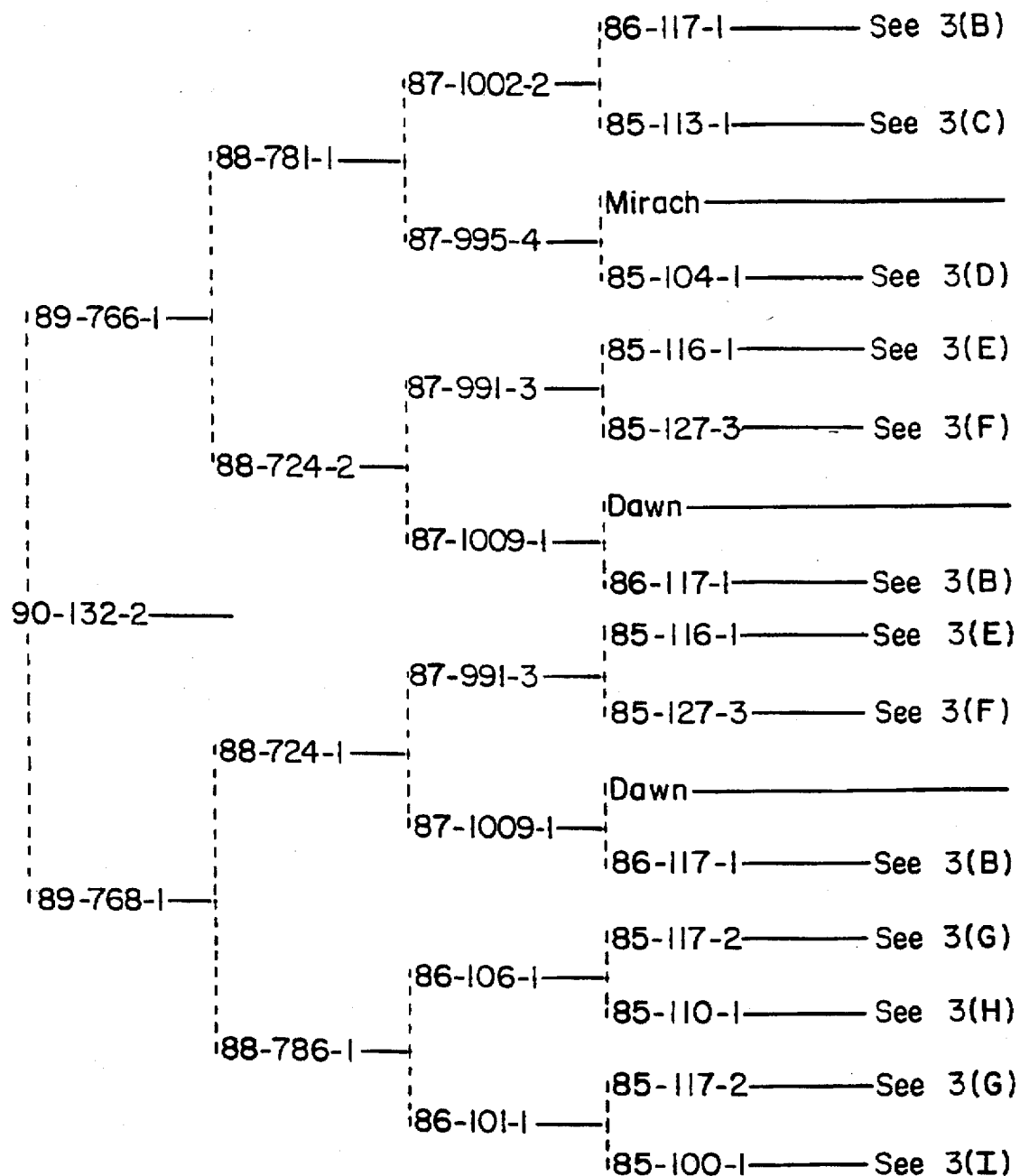
FIG. 3 (A–I). Genealogy of double-type cultivar 90-132-2. For each cross the male parent is shown above the female parent.
Figure 3B:
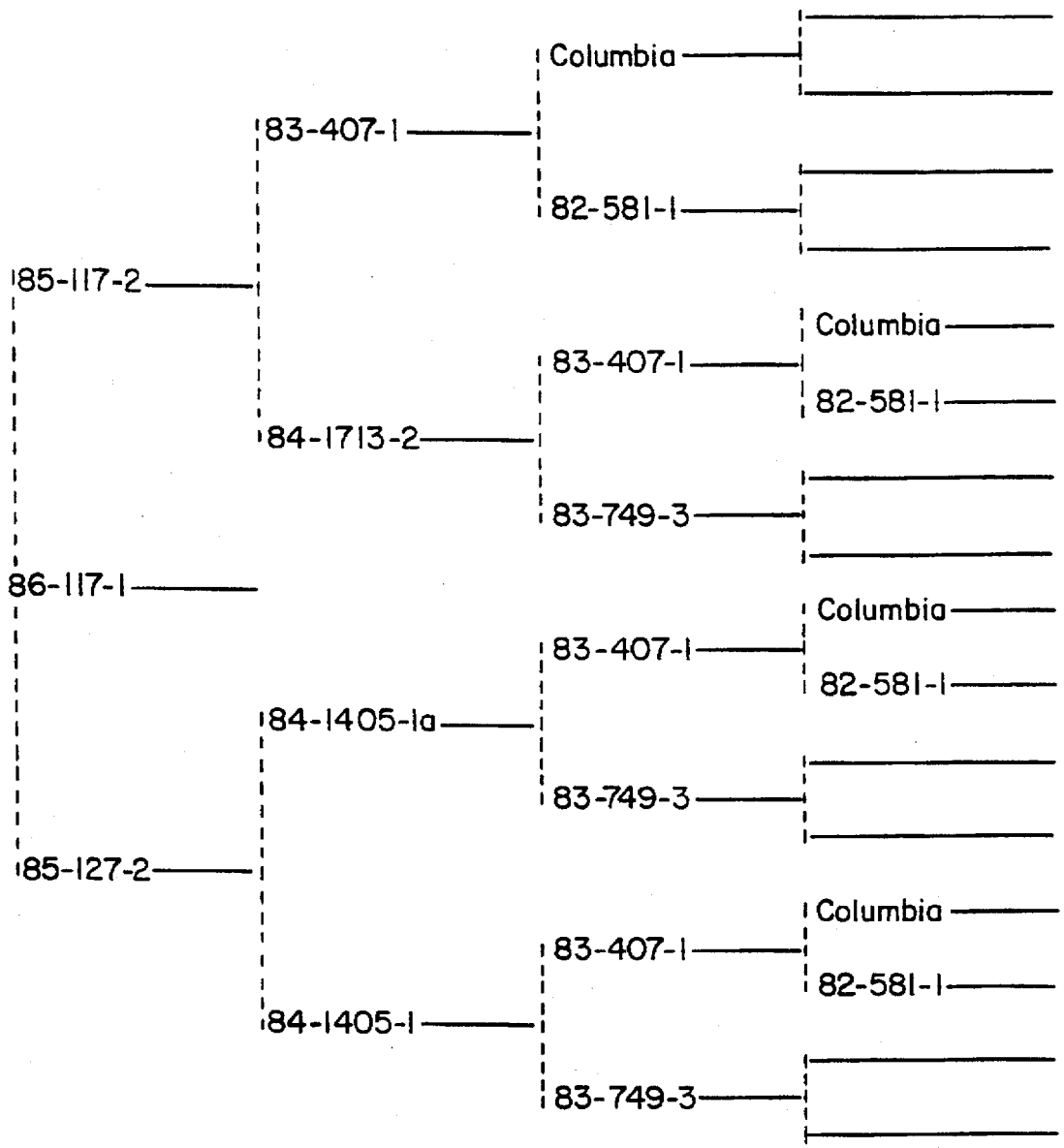
Figure 3C:
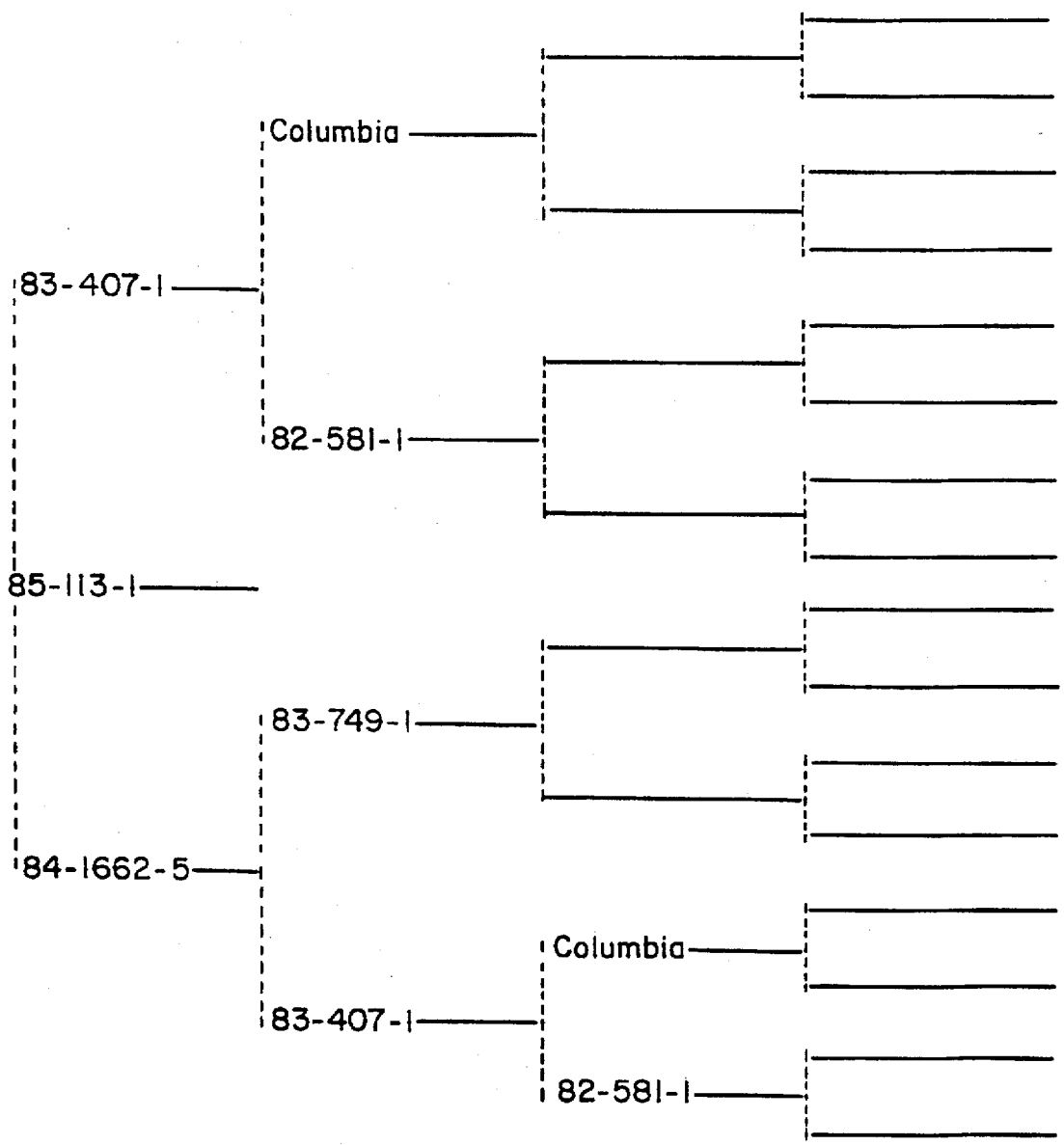
Figure 3D:
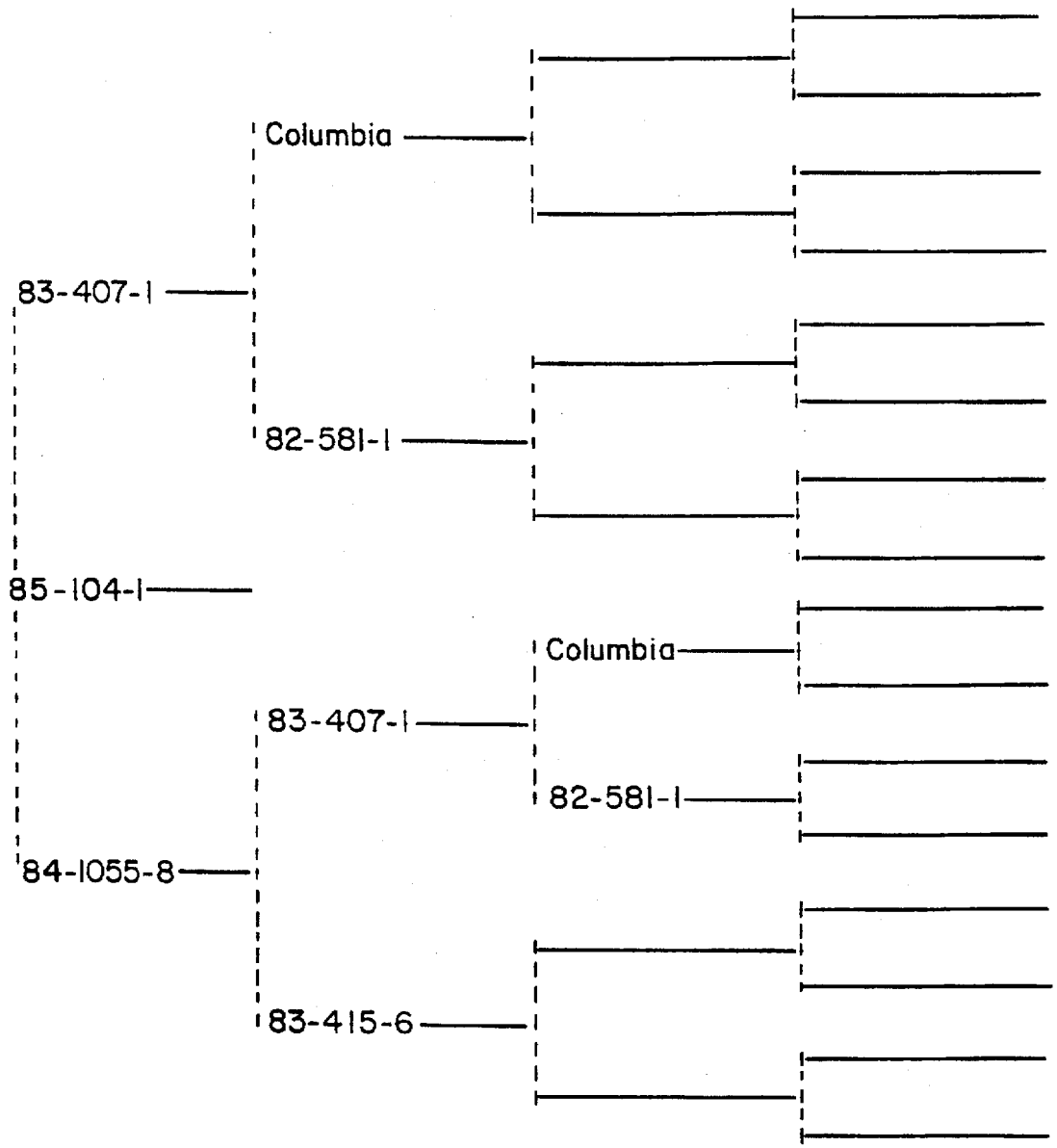
Figure 3E:
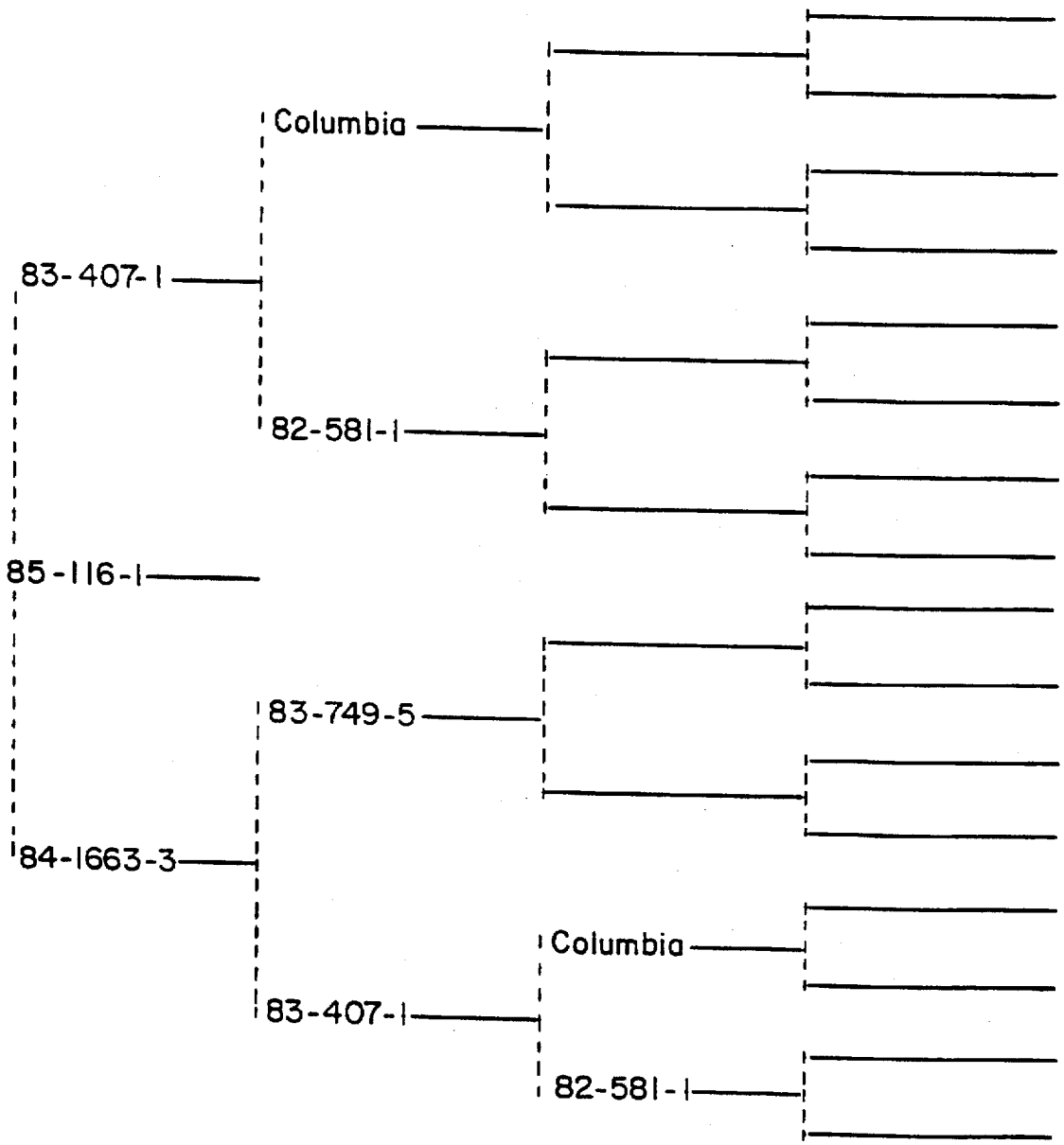
Figure 3F:
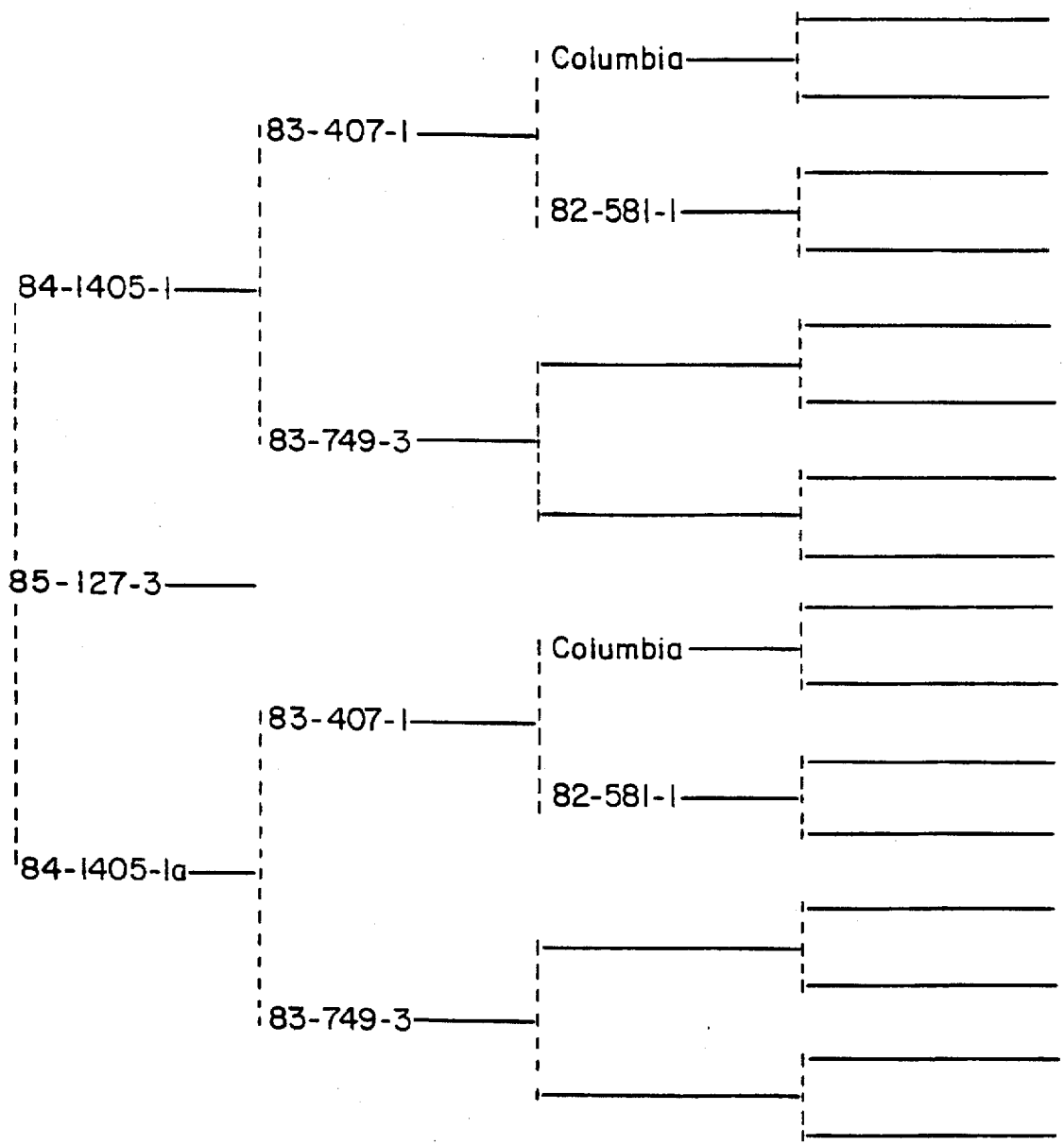
Figure 3G:
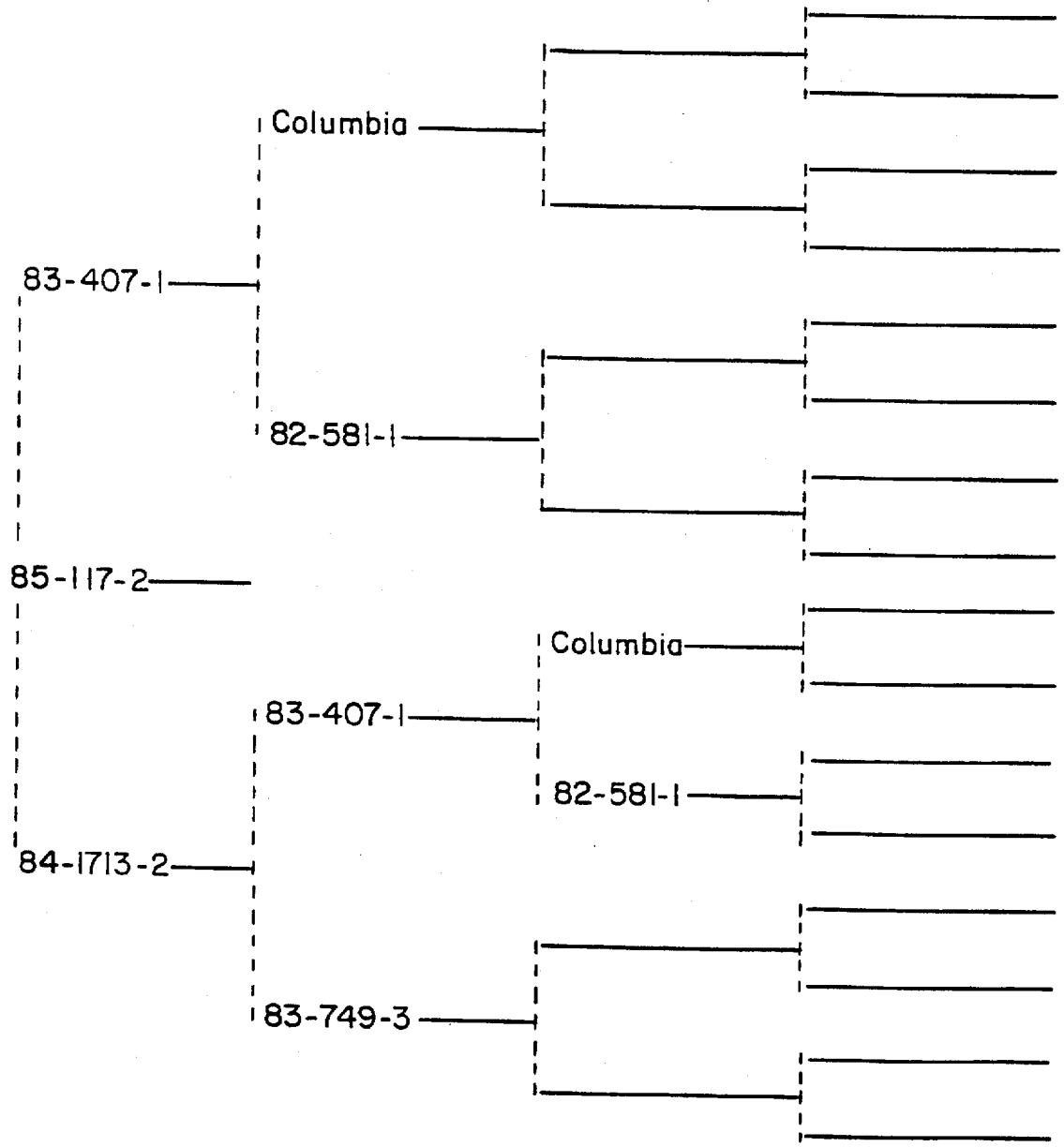
Figure 3H:
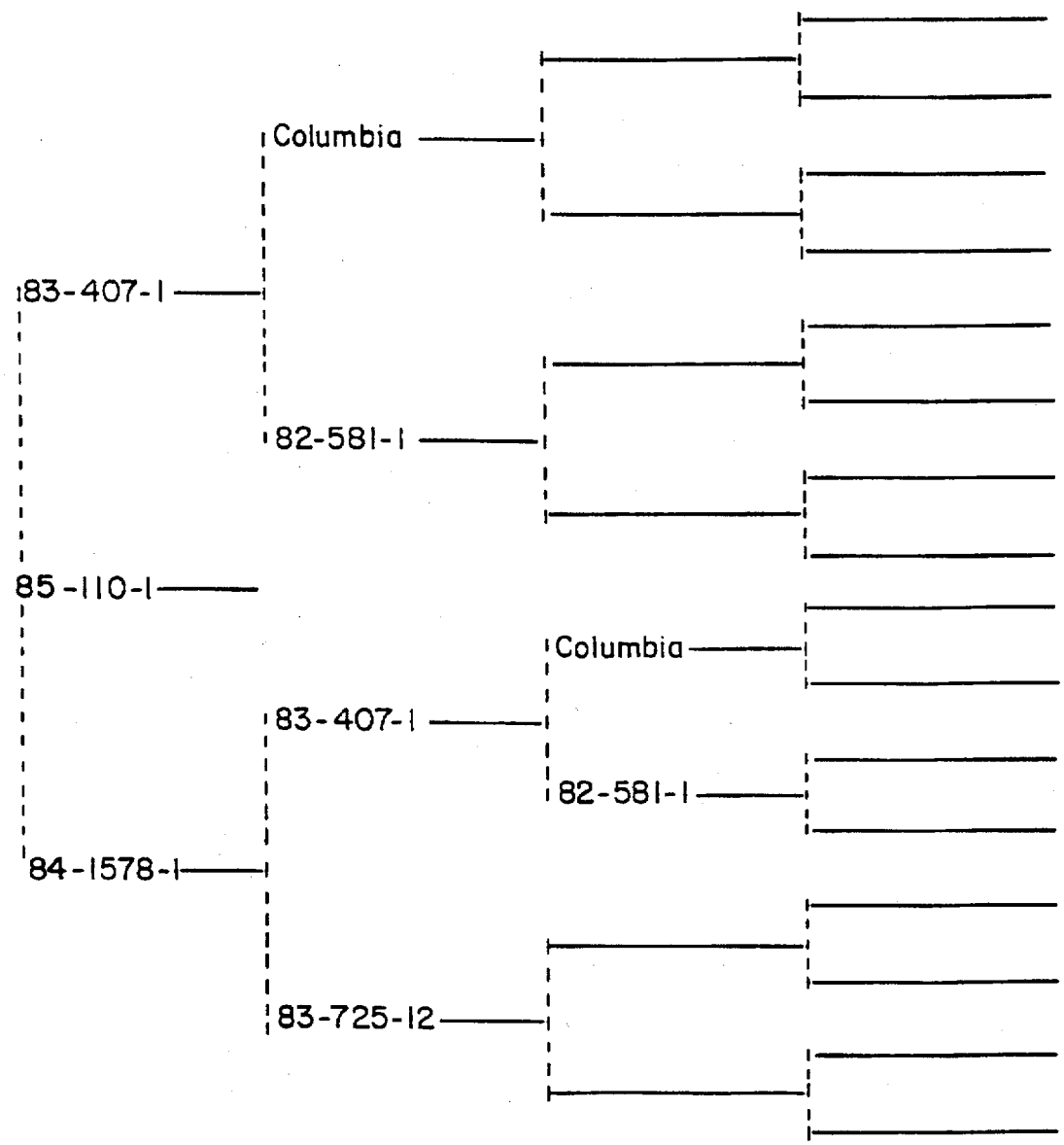
Figure 3I:
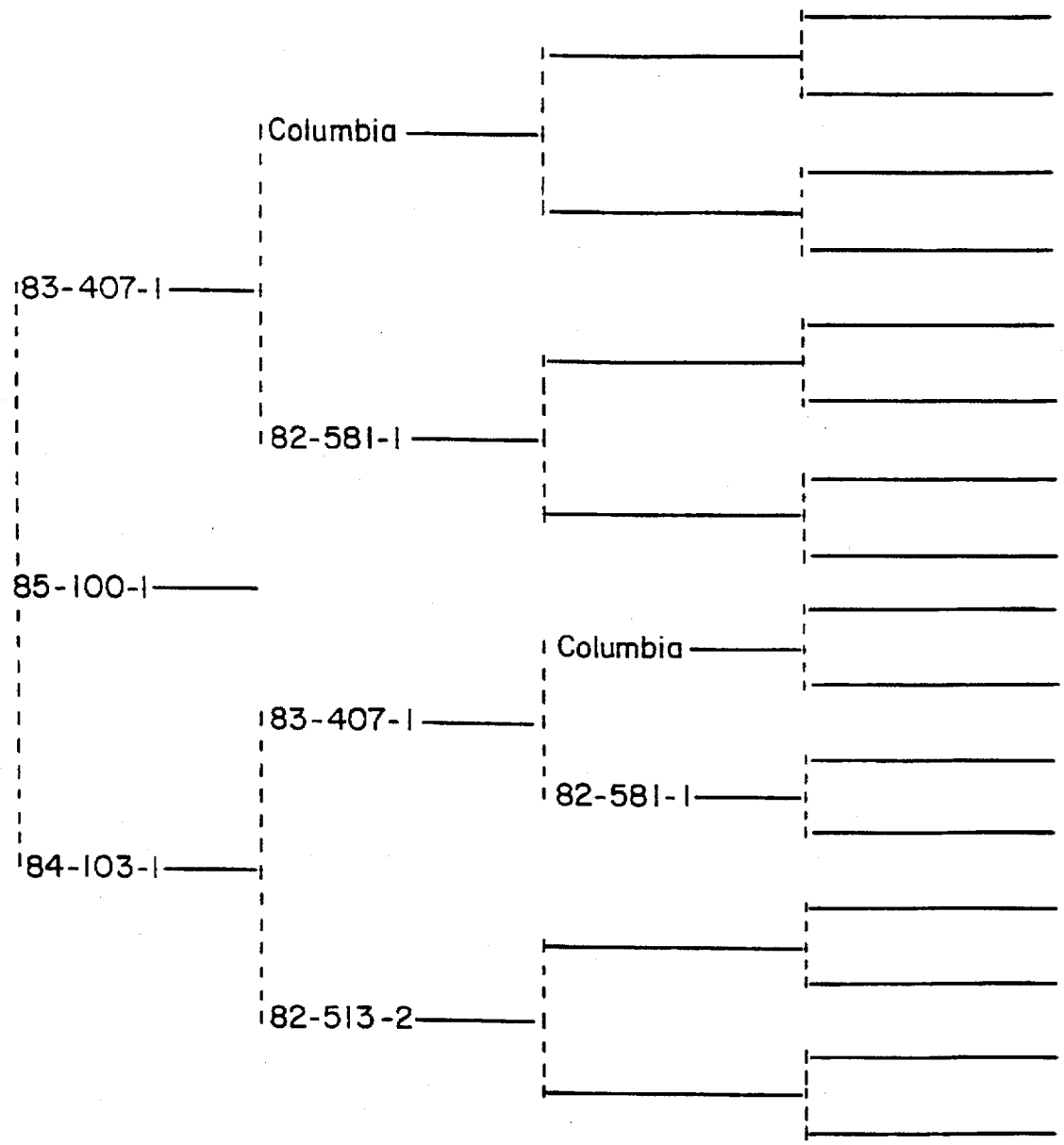
Figure 5:
FIG. 5. New Guinea Impatiens cultivar 90-139-14 which produces double-type flowers in which substantially all flowers have 9–10 petals per flower.
Figure 6:
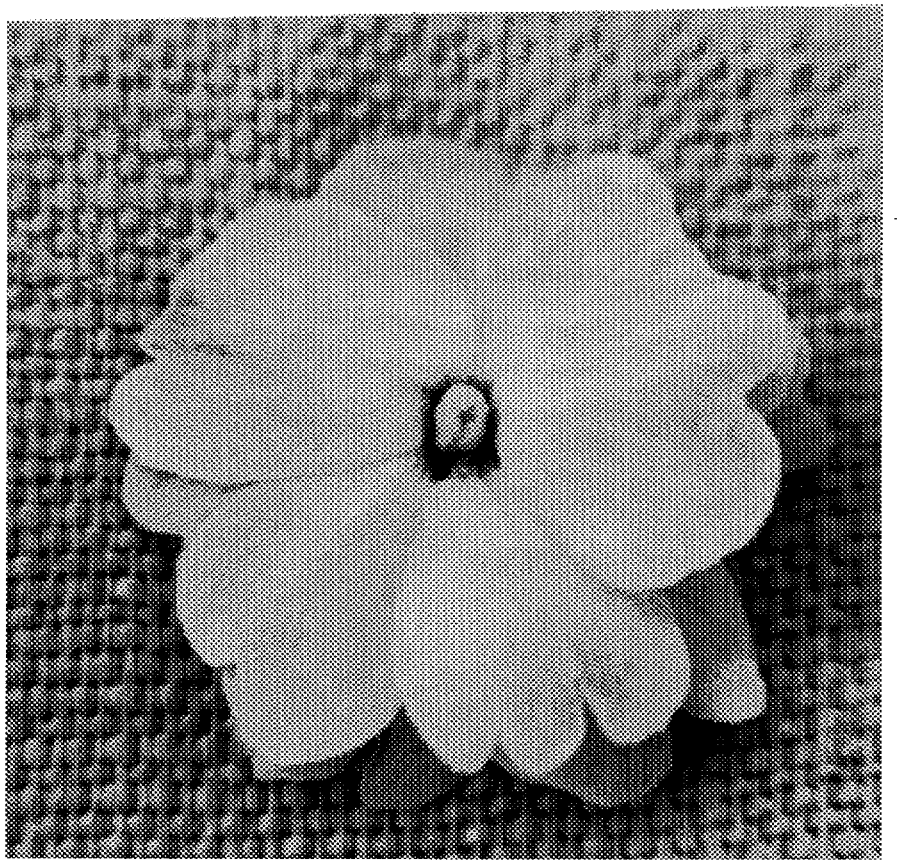
FIG. 6. A front view of a representative double-type flower from cultivar 90-132-2. The photograph is of a flower taken from 90-132-2 flowering during the summer.
Figure 7:
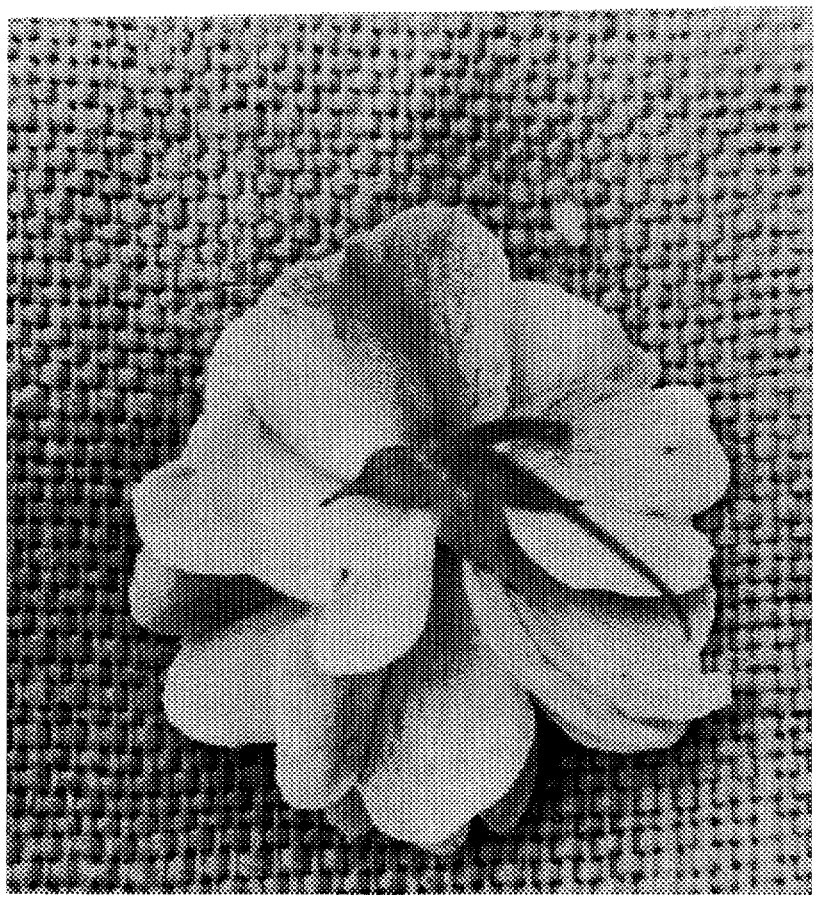
FIG. 7. A back view of a representative double-type flower from cultivar 90-132-2. The photograph is of a flower taken from 90-132-2 flowering during the summer.

Crosses were made among the best selections from generations 5 and 6. Double-flowering progeny were obtained in which substantially all the flowers in the inflorescence were double-type (generation 7). A total of 28 selections were made each of which showed stable doubleness. All but three of these selections had either 88-781-1 or 88-782-1 in their lineage. Several of these selections exhibited doubleness at high temperatures (night temperatures above 70° F. for several days) including 90-170-10, 90-132-2 and 90-139-14. Cultivar 90-132-2, isolated in generation 7 as set forth above, is described in detail in Table I and is shown in FIGS. 2, 6 and 7. The genealogy of 90-132-2 is shown in FIG. 3. Cultivar 90-139-14, isolated in generation 7 as set forth above, is described in detail in Table VII and is shown in FIG. 5. The genealogy of 90-139-14 is shown in FIG. 4.

A preferred cultivar for use as breeding stock for the transfer of the double-type characteristic to diverse single-type and semi-double-type NGI genetic backgrounds is cultivar 90-132-2. Cultivar 90-132-2 has been deposited at the American Type Culture Collection, 12301 Parklawn Drive, Rockville, Md., U.S.A., and has been accorded Accession No. 75264.

Other stable cultivars of interest were isolated through the breeding program described above. These cultivars display a great variety of phenotypes. Cultivar 90-1000-2 has white flowers that are 5 to 6 cm in diameter. Substantially all the flowers in the inflorescence have 10 full petals that lie flat when fully open. The leaves are green with cream variegation and the plant has a mounded habit. Cultivar 90-1029-1 has light pink petals with white near the eye radiating out into the petal. The flowers are 5 to 6 cm in diameter and substantially all the flowers in the inflorescence have 10 full petals that lie flat when fully open. The leaves are green without any variegation and the plant has a mounded growth habit.

Cultivar 90-1094-1 produces rose-pink flowers that are 5 to 6 cm in diameter. Substantially all the flowers in the inflorescence have 10 petals but often some of the extra petals are partial petals. As a consequence the flowers appear tufted because the partial petals tend not to lie flat. The leaves are green without variegation and the plant has a semi-upright growth habit. Cultivar 90-1129-2 produces salmon-orange flowers that are 5 to 6 cm in diameter. The inflorescence contains flowers having 7 to 10 petals. The extra petals are partial or full thereby giving the flower a tufted appearance. The leaves are green without any variegation and the growth habit of the plant is mounded.

In the manner described above, the doubleness trait has been successfully fixed in the breeding material so that doubleness can be easily and predictably bred into diverse NGI genetic backgrounds. Doubleness has been successfully combined with a large number of desirable NGI characteristics including different flower colors, growth habits, leaf colors, leaf variegations, etc. Several strategies are available by means of which doubleness can be successfully bred into diverse single-type or semi-double-type genetic backgrounds. These same strategies can be used to increase the degree of doubleness per flower or plant and to combine doubleness with other desirable NGI characteristics. A double-type plant is crossed, either as the male or female parent, to a single-type or a semi-double-type and F1 progeny are selected. The F1 progeny may include double-types. Selected progeny can be crossed to another double-type, a semi-double-type or a single-type with doubleness in its genetic background. The second double-type can be the double-type parent (backcross) or another double-type of different genetic background. Progeny are selected having one or more flowers with 7 or more petals per flower.

Alternatively, a double-type plant is crossed, either as the male or female parent, to second double-type and F1 progeny selected. The F1 progeny may include double-types. The F1 progeny can be crossed to a third double-type, a semi-double-type or a single-type with doubleness in its genetic background. The first, second or third double-type can be different or the same cultivar(s). For example, double-type selection 90-139-14 was used as either a male or female parent in crosses with three different double-type cultivars. All three crosses produced at least one double-type offspring which produced one or more flowers having at least 7 petals per flower. Of the 79 offspring screened, 60 (76%) were double-type.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLE 1

Selection of New Double-type NGI Cultivars by Means of Crossing a Double-type Cultivar (90-132-2) to a Single-type Cultivar (89-717-1) and Backcrossing to the Double-type Parent.

New double-type NGI cultivars were produced by means of crossing a selected double-type cultivar to a single-type cultivar and backcrossing to the double-type parent. NGI double-type cultivar 90-132-2 was crossed as the female parent to NGI single-type cultivar 89-717-1 as the male parent. A detailed description of 90-132-2 and 89-717-1 is contained in Tables I and II, respectively. The detailed descriptions are based on plants produced in greenhouses in Ashtabula, Ohio during the winter season of the year. Plants were grown in 15 cm pots and measurements were taken 12 weeks after rooted cuttings were planted. Height measurements were taken from the soil line of the container. The plants were grown with night temperatures at 65°–68° F. and day temperatures of 70°–75° F. The plants were grown under 3000–4000 foot candles of light. The artificial peat styrofoam soil mix was watered with a solution containing 250 ppm nitrogen, 75 ppm potassium and 250 ppm phosphorus, supplemented with trace elements. Color references were made to the Royal Horticultural Society Colour Chart except where general terms of ordinary dictionary significance are used. The phenotypes of all progeny produced from the following crosses were ascertained under the same environmental conditions and using the same methods.

TABLE I

Detailed Description of NGI 90-132-2

Parentage: NGI 90-132-2 is the Product of a controlled cross between Mikkelsen Seedling No. 89-768-1 (female) x Mikkelsen Seedling No. 89-766-1 (male).

Propagation:

| | |
|---|---|
| A. | Type cutting. Stem cuttings of 15 mm will develop to 4 to 5 cm in length within 18 to 21 days. |
| B. | Time to initiate roots. The time required to initiate roots is 8–10 days at 23° C. in summer and 10–12 days at 20° C. in winter. |
| C. | Rooting habit. The rooting habit is heavy and fibrous. |

Plant description:

| | |
|---|---|
| A. | Form. The form is semi-mounded which is self-branched but with a somewhat open branch structure. |
| B. | Growth Habit. This cultivar is intermediate in height with flowers over the top of the leaf canopy. This cultivar grows vigorously and is herbaceous. |
| C. | Foliage. The foliage is deep green with a yellow-green midrib on the top of the leaf. There is no variegation. The average mature leaf is 10 to 11 cm long and 3.5 to 4.0 cm wide. The shape of the leaf is lanceolate with an acuminate apex and acute base. The texture of the foliage is glabrous both above and below. The margins of the foliage are finely serrated and finely ciliate. The young foliage on the top side is yellow-green (146A) and on the underside yellow-green (146B). The mature foliage on the top side is yellow-green (147A) and on the underside is yellow-green (147B). The venation of the foliage is green in color and pinnate. |

Flowering description:

| | |
|---|---|
| A. | Flowering habits. Flowering is continuous from the leaf whorl and occurs in a progressive and orderly manner with one flower per leaf axil. When the last flower in a leaf whorl opens, the first flower in the leaf whorl above starts to open. It takes 5 to 7 days for a mature bud to fully open and the flower may last 2 weeks or longer depending on environmental conditions. |
| B. | Natural flowering season. Flowering is |

TABLE I-continued

Detailed Description of NGI 90-132-2

| | |
|---|---|
| | indeterminate and continuous. The quantity of flowers per plant increases with increasing levels of light. |
| C. | Flower bud description. The flower bud is ellipsoidal and flowers perfect. There is a reddish-purple cast to the spur with a green tip which is 3.0 cm on the mature bud. The throat is behind the ovary and originates from the major sepal. |
| D. | Flowers borne. Each flower has an individual green pedicel which is 3.0 to 3.5 cm long from the whorl typically containing 6 leaves. Flowering occurs progressively around the whorl as buds and leaves develop. It is normal to find one flower per leaf axil. |
| E. | Quantity of flowers. This cultivar is highly floriferous because of the self-branching nature of the plant. The flowers are long-lasting. Substantially all the flowers per plant are double-type having 8–10 petals per flower. |
| F. | Diameter of flowers. The flowers are 6.0 to 6.5 centimeters in diameter. |
| G. | Petals. Substantially all the flowers per plant are double-type having 8–10 petals per flower. The petals are heart-shaped with the keel oi the bottom whorl of petals being the largest. The color of the top side of the petals in winter when opening is white (155B) near the margins with a blush as deep as 56A in the red group. This fades to larger areas of 155B and a blush of 56B and 56C. The color of the underside of the petal in winter is mostly 155B. Under summer conditions the pink coloration intensifies both on the top side and bottom side of the flower petals. The color of the top side in summer on fully opened flowers ranges from areas as deep as 55B to 56A in the red group to areas of 155D in the white group resulting in a streaking effect. The color on the underside in the summer ranges from 55B to 56A in a streaking effect to small area of 155D usually near the edge of the petals. The midrib of the petals is 56A and the area near the midrib of the standard is 146A in winter and 146C in summer. There is only one true standard in the lower whorl and there is no petal in the upper whorl that is like a standard. There are two sets of wing petals. The keel of the lower whorl has 2 normal keel petals and the upper whorl has 2 keel petals together with a third keel-like petal. |
| H. | Reproductive organs. The flower contains 5 stamens. The anther shape is hooded with a cream color and the pollen color is cream. The pistils have a stigma with 5 segmented columns which are greenish-white in color. The style color is greenish-white. The ovaries number 5 and are 6 mm in size at maturity and green in color. |
| I. | Disease resistance. This cultivar does not appear to be particularly sensitive to disease or insect infestation. |

TABLE II

Detailed Description of NGI 89-717-1

Parentage: NGI 89-717-1 is the product of a controlled cross between Mikkelsen Seedling No. 88-690-2 (female) x Mikkelsen Seedling No. 86-171-3 (male).

Propagation:

| | |
|---|---|
| A. | Type cutting. Stem cuttings of 15 mm will |

TABLE II-continued

Detailed Description of NGI 89-717-1 develop to 4 to 5 cm in length within 18 to 21 days.
- B. Time to initiate roots. The time required to initiate roots is 8–10 days at 23° C. in summer and 10–12 days at 20° C. in winter.
- C. Rooting habit. The rooting habit is heavy, fibrous, and numerous.

Plant description:

- A. Form. The form is compact and mounded with excellent self-branching.
- B. Growth Habit. This cultivar flowers over the top of the leaf canopy, grows vigorously and is herbaceous.
- C. Foliage. The foliage is dark green with cream variegation around the reddish midrib at the basal end of the leaf. The average mature leaf is 10 to 11 cm long and 4.0 to 4.5 cm wide. The shape of the leaf is lanceolate with an acuminate apex and acute base. The texture of the foliage is glabrous on both the upper and lower surfaces. The margins of the foliage are finely serrated and finely ciliate. The young foliage on the top side is yellow-green (146A) and on the underside is yellow-green (146B). The mature foliage on the top side is yellow-green (147A) with variegation (13B) and the color on the underside is yellow-green (147B). The venation of the foliage is green in color and pinnate.

Flowering description:

- A. Flowering habits. Flowering is continuous from the leaf whorl and occurs in a progressive and orderly manner with usually two flowers per leaf axil. All first flowers in a whorl open before the second flower in the leaf axil of the whorl. When second flowers of a leaf axil start to open the first flower of a leaf axil of the whorl above starts to open. It takes 5 to 7 days for a mature bud to fully open and the flower may last 2 weeks or longer depending on environmental conditions.
- B. Natural flowering season. Flowering is indeterminate and continuous. The quantity of flowers per plant increases with increasing levels of light.
- C. Flower bud description. The flower bud is ellipsoidal and flowers perfect. The spur is reddish-purple with a green tip up to 4.5 cm long on the mature bud. The throat is behind the ovary and originates from the major sepal.
- D. Flowers borne. Each flower has an individual reddish pedicel which is 4.0 cm long from a whorl of 4 to 5 leaves. Flowering occurs progressively around the whorl as buds and leaves develop. Most leaf axils have two flowers.
- E. Quantity of flowers. This cultivar is highly floriferous because of the self-branching nature of the plant. The flowers are long-lasting and with 2 flowers per leaf axil there are flowers open at 3 leaf whorls at a time.
- F. Diameter of flowers. The flowers are 6.0 to 6.5 centimeters in diameter.
- G. Petals. The number of petals per flower is 5. The petals are heart-shaped with the standard being the largest. The color of the top side of the petals in winter when opening is in the red-purple group (74A). This color fades to 74B. The color of the underside of the petal is also in the red-purple group (74C). The standard is 4.0 cm wide and 3.0 cm long with 2 unequal lobes that are shallow cut. The wings are 2.25 cm and 3.5 cm long with 2 unequal lobes that are shallow cut. The keel is 3.0 cm wide and 3.0 cm long with 2 unequal lobes that are deeply cut.
- H. Reproductive organs. The flower contains 5 stamens. The anther shape is hooded and its color is cream with a reddish tint. The pollen color is cream. The pistils have a stigma with 5 segmented columns which are greenish-white in color. The style color is whitish-green. The ovaries number 5 and are 6 mm in size at maturity and green in color.
- I. Disease resistance. This cultivar does not appear to be particularly sensitive to disease or insect infestation.

Seven semi-doubles, having one or more flowers with 6 full or partial petals per flower, and 12 single-type progeny were observed among the 18 F1 progeny obtained from the cross of 90-132-2 to 89-717-1. A total of 12 backcrosses were made to the double-type parent 90-132-2. Six different F1 progeny were each used once as the male and once as the female parent. For each of the progeny produced from these backcrosses, the petal number of the flower(s) with the highest number of petals per flower was recorded. Both full and partial petals were counted. The results are shown in Table III. Of the 482 progeny obtained, 72 (14.9%) were single-type, 40 (8.2%) were semi-double, 344 (71.4%) were double-type, and 26 (5.4%) failed to bloom. A significant number of plants produced one or more flowers with 12 petals per flower (1.7%).

TABLE III

Analysis of Progeny Resulting from Backcross of F1 Progeny to the Double-Type Parent 90-132-2:
Number of Progeny in Each Petal Number Category

| FAMILY | FEMALE | x | MALE | HIGHEST NUMBER OF PETALS/FLOWER ||||||||| NO BLOOM | TOTAL PLANTS |
| | | | | 5 | 6 | 7 | 8 | 9 | 10 | 11 | 12 | | |
| --- | --- | --- | --- | --- | --- | --- | --- | --- | --- | --- | --- | --- | --- |
| 91-1300 | 90-132-2 | x | 90-1219-1 | 0 | 3 | 12 | 5 | 5 | 9 | 1 | 0 | 1 | 36 |
| 91-1301 | 90-132-2 | x | 90-1219-2 | 4 | 2 | 4 | 5 | 1 | 4 | 1 | 1 | 5 | 27 |
| 91-1302 | 90-132-2 | x | 90-1219-4 | 10 | 10 | 9 | 5 | 4 | 3 | 0 | 0 | 3 | 44 |
| 91-1303 | 90-132-2 | x | 90-1219-8 | 3 | 3 | 10 | 7 | 7 | 11 | 4 | 2 | 1 | 48 |
| 91-1304 | 90-132-2 | x | 90-1219-9 | 4 | 3 | 24 | 11 | 6 | 7 | 2 | 1 | 0 | 58 |
| 91-1305 | 9P-132-2 | x | 90-1219-10 | 11 | 4 | 12 | 9 | 3 | 5 | 0 | 1 | 3 | 48 |
| 91-1306 | 90-1219-1 | x | 90-132-2 | 4 | 3 | 12 | 4 | 2 | 3 | 4 | 0 | 1 | 33 |
| 91-1307 | 90-1219-2 | x | 90-132-2 | 1 | 1 | 11 | 8 | 7 | 5 | 0 | 0 | 7 | 40 |

TABLE III-continued

Analysis of Progeny Resulting from Backcross of F1 Progeny to the Double-Type Parent 90-132-2:
Number of Progeny in Each Petal Number Category

| FAMILY | FEMALE | x | MALE | HIGHEST NUMBER OF PETALS/FLOWER | | | | | | | | NO BLOOM | TOTAL PLANTS |
|---|---|---|---|---|---|---|---|---|---|---|---|---|---|
| | | | | 5 | 6 | 7 | 8 | 9 | 10 | 11 | 12 | | |
| 91-1309 | 90-1219-4 | x | 90-132-2 | 9 | 5 | 8 | 2 | 0 | 1 | 0 | 0 | 1 | 26 |
| 91-1310 | 90-1219-8 | x | 90-132-2 | 3 | 1 | 9 | 6 | 4 | 6 | 2 | 0 | 0 | 31 |
| 91-1312 | 90-1219-9 | x | 90-132-2 | 11 | 2 | 19 | 10 | 4 | 4 | 0 | 2 | 0 | 52 |
| 91-1313 | 90-1219-10 | x | 90-132-2 | 12 | 3 | 10 | 4 | 4 | 0 | 1 | 1 | 4 | 39 |
| TOTAL | | | | 72 | 40 | 140 | 76 | 47 | 58 | 15 | 8 | 26 | 482 |
| % TOTAL | | | | 14.9 | 8.2 | 29.0 | 15.8 | 9.9 | 12.1 | 3.1 | 1.7 | 5.4 | |

The phenotypes of the progeny produced in backcross family 91-1303 are shown in Table IV. These progeny resulted from the cross of 90-132-2 as the female and 90-1219-8 as the male. Petal number per flower, flower color, and leaf variegation assorted independently. A wide range of different flower colors were combined with double-type flowers and foliage that was either solid or variegated.

TABLE IV

Phenotypes of Family 91-1303 Resulting from the Backcross of Double-type Parent 90-132-2 to F1 Progeny 90-1219-8.

| PROGENY | HIGHEST NUMBER OF PETALS/FLOWER | FLOWER COLOR[1] | LEAF COLOR[2] | LEAF VARIEGATION[3] |
|---|---|---|---|---|
| 1 | 6 | S | G | S |
| 2 | 6 | S | G | S |
| 3 | 10 | W | G | V |
| 4 | 12 | W | G | V |
| 5 | 6 | B | G | S |
| 6 | 9 | S | G | S |
| 7 | 10 | S | G | V |
| 8 | 11 | B | G | V |
| 9 | 7 | P | G | S |
| 10 | 7 | B | G | S |
| 11 | 8 | R | G | V |
| 12 | 10 | LP | G | S |
| 13 | 10 | W | G | S |
| 14 | 10 | P | G | V |
| 15 | 11 | W | G | V |
| 16 | 9 | P | G | S |
| 17 | 11 | B | G | S |
| 18 | 9 | P | G | S |
| 19 | 9 | P | G | V |
| 20 | 10 | P | G | S |
| 21 | 9 | R | G | S |
| 22 | 10 | S | G | S |
| 23 | 7 | P | G | V |
| 24 | 7 | LP | G | S |
| 25 | 8 | B | G | S |
| 26 | 8 | S | G | S |
| 27 | 7 | W | G | S |
| 28 | 7 | P | G | S |
| 29 | 7 | S | G | V |
| 30 | 11 | P | G | V |
| 31 | 8 | S | G | V |
| 32 | 9 | W | G | S |
| 33 | 12 | P | G | S |
| 34 | 10 | P | G | V |
| 35 | 10 | S | G | S |
| 36 | 8 | P | G | V |
| 37 | 8 | S | G | S |
| 38 | 10 | W | G | V |
| 39 | 8 | W | G | S |
| 40 | 7 | B | G | S |
| 41 | 7 | S | G | V |
| 42 | 5 | S | G | S |
| 43 | 5 | P | G | V |

TABLE IV-continued

Phenotypes of Family 91-1303 Resulting from the Backcross of Double-type Parent 90-132-2 to F1 Progeny 90-1219-8.

| PROGENY | HIGHEST NUMBER OF PETALS/FLOWER | FLOWER COLOR[1] | LEAF COLOR[2] | LEAF VARIEGATION[3] |
|---|---|---|---|---|
| 44 | 5 | P | G | S |
| 45 | 10 | R | G | S |
| 46 | 9 | P | G | V |
| 47 | 7 | S | G | V |
| 48 | 0 | — | — | — |

[1] B = Blush
LP = Light Pink
P = Pink
R = Rose
S = Salmon
W = White
[2] G = Green
[3] S = Solid
V = Variegation The double-type parent 90-132-2, having white flowers with a pink blush and no leaf variegation was therefore successfully crossed to a single-type, having purple flowers and leaf variegation. Following backcrossing of F1 progeny to the double-type parent, selections were obtained exhibiting diverse phenotypes. These plants included those with double-type flowers with colors that included salmon, blush, pink, rose, and light pink. Plants producing double-type flowers and variegated leaves were also obtained. Additionally, backcrossing to the double-type parent gave rise to plants having an inflorescence that included flowers with increased petal number per flower as compared to the double-type parent.

EXAMPLE 2

Selection of New Double-type NGI Cultivars by Means of Crossing a Double-type Cultivar (90-132-2) to a Single-type Cultivar (89-717-1) and Sibcrossing Among the F1 Progeny.

In addition to backcrossing, sibcrossing was undertaken among F1 progeny produced from the cross of 90-132-2 to 89-717-1, described above. The sib 90-1219-8 was used as the female in a cross to sib 90-1219-2 as the male. The phenotypes of the progeny produced in sibcross family 91-1311 are shown in Table V. For each of the progeny produced from these sibcrosses, the petal number of the flower(s) with the highest number of petals per flower was recorded. Both full and partial petals were counted.

Petal number per flower, flower color, and leaf variegation assorted independently. A wide range of different flower colors were combined with double-type flowers and foliage that was either solid or variegated.

TABLE V

Phenotype of Family 91-1311 Resulting from Sibcrossing F1 Progeny 90-1219-8 x 90-1219-2.

| PRO-GENY | HIGHEST NUMBER OF PETALS/FLOWER | FLOWER COLOR[1] | LEAF COLOR[2] | LEAF VARIEGA-TION[3] |
|---|---|---|---|---|
| 1 | 8 | S | G | S |
| 2 | 9 | L | G | S |
| 3 | 7 | S | G | S |
| 4 | 8 | P | G | V |
| 5 | 7 | W | G | V |
| 6 | 6 | S | G | S |
| 7 | 9 | R | G | S |
| 8 | 5 | P | G | V |
| 9 | 8 | O | G | S |
| 10 | 6 | P | G | V |
| 11 | 5 | R | G | V |
| 12 | 5 | RD | G | V |
| 13 | 5 | P | G | V |
| 14 | 5 | L | G | S |
| 15 | 7 | P | G | V |
| 16 | 5 | B | G | S |
| 17 | 7 | R | G | V |
| 18 | 5 | P | G | S |
| 19 | 5 | P | G | V |
| 20 | 5 | R | G | V |
| 21 | 5 | L | G | V |
| 22 | 5 | O | G | S |
| 23 | 5 | P | G | V |
| 24 | 5 | O | G | V |
| 25 | 5 | S | G | S |
| 26 | 5 | O | G | S |
| 27 | 5 | R | G | S |
| 28 | 5 | P | G | S |
| 29 | 0 | — | — | — |
| 30 | 5 | B | G | V |
| 31 | 7 | P | G | V |

[1]B = Blush
L = Lavender
LP = Light Pink
P = Pink
RD = Red
R = Rose
S = Salmon
W = White
[2]G = Green
[3]S = Solid
V = Variegation

EXAMPLE 3

Selection of New Double-type NGI Cultivars by Means of Crossing a Single-type Cultivar (89-430-3) to Double-type Cultivar (90-139-14) and Backcrossing to the Double-type Parent.

New double-type NGI cultivars were produced by means of crossing a selected double-type cultivar to a single-type cultivar and backcrossing to the double-type parent. NGI single-type cultivar 89-430-3 was crossed as the female parent to NGI double-type cultivar 90-139-14 as the male parent. Additionally, the reciprocal cross was made in which the single-type cultivar 89-430-3 was used as the male parent and the double-type cultivar 90-139-14 was used as the female parent. A detailed description of cultivars 89-430-3 and 90-139-14 is contained in Tables VI and VII, respectively. The detailed descriptions are based on plants produced in greenhouses in Ashtabula, Ohio during the winter season of the year. Plants were grown in 15 cm pots and measurements were taken 12 weeks after rooted cuttings were planted. Height measurements were taken from the soil line of the container. The plants were grown with night temperatures at 65°–68° F. and day temperatures of 70°–75° F. The plants were grown under 3000–4000 foot candles of light. The artificial peat styrofoam soil mix was watered with a solution containing 250 ppm nitrogen, 75 ppm potassium and 250 ppm phosphorus, supplemented with trace elements. Color references were made to the Royal Horticultural Society Colour Chart except where general terms of ordinary dictionary significance are used. The phenotypes of all progeny produced from the following crosses were ascertained under the same environmental conditions and using the same methods.

TABLE VI

Detailed Description of NGI 89-430-3

Parentage: NGI 89-430-3 is the product of a controlled cross between Mikkelsen Seedling No. 88-690-2 (female) x Mikkelsen Seedling No. 86-171-3 (male).
Propagation:

A. Type cutting. Stem cuttings of 15 mm will develop to 4 to 5 cm in length within 18 to 21 days.
B. Time to initiate roots. The time required to initiate roots is 8–10 days at 23° C. in summer and 10–12 days at 20° C. in winter.
C. Rooting habit. The rooting habit is heavy, fibrous, and numerous.

Plant description:

A. Form. The form is compact and mounded with excellent self-branching.
B. Growth Habit. This cultivar flowers over the top of the leaf canopy, grows vigorously and is herbaceous.
C. Foliage. The foliage is dark green with cream variegation around the reddish midrib at the basal end of the leaf. The average mature leaf is 10 to 11 cm long and 4.0 to 4.5 cm wide. The shape of the leaf is lanceolate with an acuminate apex and acute base. The texture of the foliage is glabrous on both the upper and lower surfaces. The margins of the foliage are finely serrated and finely ciliate. The young foliage on the top side is yellow-green (146A) and on the underside is yellow-green (146B). The mature foliage on the top side is yellow-green (147A) with variegation (13B) and on the underside is yellow-green (147B). The venation of the foliage is green in color and pinnate.

Flowering description:

A. Flowering habits. Flowering is continuous from the leaf whorl and occurs in a progressive and orderly manner with usually two flowers per leaf axil. All first flowers in a whorl open before the second flower in the leaf axil of the whorl. When second flowers of a leaf axil start to open the first flower of a leaf axil of the whorl above starts to open. It takes 5 to 7 days for a mature bud to fully open and the flower may last 2 weeks or longer depending on environmental conditions.
B. Natural flowering season. Flowering is indeterminate and continuous. The quantity of flowers per plant increases with increasing levels of light.
C. Flower bud description. The flower bud is ellipsoidal and flowers perfect. The spur is reddish-purple with a green tip up to 4.5 cm long on the mature bud. The throat is behind the ovary and originates from the major sepal.
D. Flowers borne. Each flower has an individual green pedical which is 4.0 to 4.5 cm long from a whorl of usually 4, but varying from 3 to 5 leaves. Flowering occurs progressively around the whorl as buds and leaves develop. One flower per leaf axil is normal.
E. Quantity of flowers. This cultivar is highly floriferous because of the self-branching

TABLE VI-continued

Detailed Description of NGI 89-430-3 nature of the plant. The flower are long-lasting and therefore many are open on the plant at one time.

F. Diameter of flowers. The flowers are 5.0 to 5.5 centimeters in diameter.

G. Petals. The number of petals per flower is 5. The petals are heart-shaped with the two keels being the largest. The color of the top side of the petals in winter when opening is in the red-purple group on the outer areas (67B to 74B) and red-purple near the center of the petals (57A). This color fades to 67C to 74C in the outer areas of the petals and 57B at the center of the petals. The color of the underside of the petal is 67C in the outer areas and 57A in the center of the petal. The standard is 3.0 cm wide and 2.0 cm long with 2 equal lobes and almost no cut. The wings are 2.0 cm and 2.5 cm long with 2 equal lobes that have an intermediate cut. The keel is 3.5 cm wide and 3.0 cm long with 2 unequal lobes that are deeply cut.

H. Reproductive organs. The flower contains 5 stamens. The anther shape is hooded and its color is cream with a heavy reddish-purple tint. The pollen color is cream. The pistils have a stigma with 5 segmented columns which are reddish-purple in color. The style color is reddish-purple. The ovaries number 5; are 6 mm in size at maturity; and are reddish-purple in color.

I. Disease resistance. This cultivar does not appear to be particularly sensitive to disease or insect infestation.

TABLE VII

Detailed Description of NGI 90-139-14

Parentage: NGI 90-139-14 is the product of a controlled cross between Mikkelsen Seedling No. 88-782-1 (female) x Mikkelsen Seedling No. 89-812-2 (male).

Propagation:

A. Type cutting. Stem cuttings of 15 mm will develop to 4 to 5 cm in length within 18 to 21 days.

B. Time to initiate roots. The time required to initiate roots is 8–10 days at 23° C. in summer and 10–12 days at 20° C. in winter.

C. Rooting habit. The rooting habit is abundant, heavy, and fibrous.

Plant description:

A. Form. The form is compact and mounded with excellent self-branching.

B. Growth Habit. This cultivar flowers over the top of the leaf canopy, grows vigorously and is herbaceous.

C. Foliage. The foliage is dark green with purplish cast with reddish purple midrib, petiole and underside of leaf, and no variegation. The average mature leaf is 10 to 11 cm long and 3.5 to 4.0 cm wide. The shape of the leaf is lanceolate with an acuminate apex and acute base. The texture of the foliage is glabrous on both the upper and lower surfaces. The margins of the foliage are slightly serrated and finely ciliate. The young foliage on the top side is yellow-green (147A) and on the underside has a grayed purple cast (183D). The mature foliage on the top side is yellow-green (147A) and on the underside has a grayed purple cast (183D). The

TABLE VII-continued

Detailed Description of NGI 90-139-14 venation of the foliage has a reddish cast and is pinnate.

Flowering description:

A. Flowering habits. Flowering is continuous from the leaf whorl and occurs in a progressive and orderly manner with one flower per leaf axil. When the last flower in a leaf whorl opens, the first flower in the leaf whorl above starts to open. It takes 5 to 7 days for a mature bud to fully open and the flower may last 2 weeks or longer depending on environmental conditions.

B. Natural flowering season. Flowering is indeterminate and continuous. The quantity of flowers per plant increases with increasing levels of light.

C. Flower bud description. The flower bud is ellipsoidal and flowers perfect. The spur is green with a deeper green tip up to 4.5 cm long on the mature bud. The throat is behind the ovary and originates from the major sepal.

D. Flowers borne. Each flower has an individual green pedicel from a whorl of 4 to 5 leaves. Flowering occurs progressively around the whorl as buds and leaves develop. One flower per leaf axil is normal.

E. Quantity of flowers. This cultivar is highly floriferous because of the self-branching nature of the plant. The flowers are long-lasting. Substantially all the flowers are double-type with 9–10 petals per flower.

F. Diameter of flowers. The flowers are 5.0 to 6.0 centimeters in diameter.

G. Petals. Substantially all the flowers are double-type with 9–10 petals per flower. The petal number may vary because the keel-like petal of the upper whorl is sometimes lost. The petals are heart-shaped with the keel of the bottom whorl of petals being the largest. The color of the top side of the petals in winter when opening is in the white group (155A) near the margins to the red group (54B) in the eye region of the flower and the midrib of the petal with shading (54C-D) between. This color fades to 155A, 54C-D. The color of the underside of the petal is in the white group (155A) near the margins to the red group (51A) near the midrib. There is only one true standard in the lower whorl. There is no petal in the upper whorl that is like a standard. There are two sets of wing petals. The lower whorl has two normal type keel petals and the upper whorl has two keel petals plus a third that appears keel-like.

H. Reproductive organs. The flower contains 5 stamens. The anther shape is hooded and its color is cream with a reddish purple tint. The pollen color is cream. The pistils have a stigma with 5 segmented columns which are reddish purple in color. The style color is reddish purple. The ovaries number 5 and are 5 mm in size at maturity and green with a reddish cast in color.

I. Disease resistance. This cultivar does not appear to be particularly sensitive to disease or insect infestation.

A total of 2 single-types and 1 semi-double-type were obtained from the cross of 89-430-3 as the female to 90-139-14 as the male. Two different F1 progeny were each used once, as both a male and female, in backcrosses to the double-type parent. The results of these backcrosses are shown in Table VIII. For each of the progeny produced from these backcrosses, the petal number of the flower(s) with the largest number of petals per flower was recorded. Both full and partial petals were counted. A total of 181 backcross progeny were analyzed. Of these 29 (16.0%) were single-type, 30 (16.6%) were semi-double-type, 116 (64.1%) were double-type and 6 (3.3%) failed to produced any bloom.

TABLE VIII

Analysis of Progeny Resulting from Backcross of F1 Plants to the Double-type Parent 90-139-14: Number of Progeny in Each Petal Number Category.

| FAMILY | FEMALE | x | MALE | HIGHEST NUMBER OF PETALS/FLOWER | | | | | | | | NO BLOOM | TOTAL PLANTS |
|---|---|---|---|---|---|---|---|---|---|---|---|---|---|
| | | | | 5 | 6 | 7 | 8 | 9 | 10 | 11 | 12 | | |
| 91-1318 | 90-139-14 | x | 90-1214-2 | 5 | 6 | 8 | 4 | 7 | 8 | 2 | 0 | 1 | 41 |
| 91-1319 | 90-139-14 | x | 90-1214-3 | 5 | 8 | 13 | 5 | 1 | 3 | 1 | 0 | 2 | 38 |
| 91-1321 | 90-1214-2 | x | 90-139-14 | 12 | 7 | 13 | 5 | 6 | 5 | 1 | 1 | 2 | 52 |
| 91-1322 | 90-1214-3 | x | 90-139-14 | 7 | 9 | 14 | 8 | 6 | 3 | 2 | 0 | 1 | 50 |
| | TOTAL | | | 29 | 30 | 48 | 22 | 20 | 19 | 6 | 1 | 6 | 181 |
| | % TOTAL | | | 16.0 | 16.6 | 26.5 | 12.2 | 11.0 | 10.5 | 3.3 | 0.6 | 3.3 | |

The phenotypes of the progeny produced in backcross family 91-1319 are shown in Table IX. These progeny resulted from the cross of 90-139-14 as the female to 90-1214-3 as the male. For each of the progeny produced from this backcross, the petal number of the flower(s) with the highest number of petals was recorded. Both full and partial petals were counted. Petal number per flower, flower color, leaf color and leaf variegation assorted independently. The cultivars produced in this backcross exhibited a wide range of different flower colors combined with double-type flowers and foliage that was either solid or variegated.

TABLE IX

Phenotypes of Family 91-1319 Resulting from the Backcross of F1 Progeny 90-1214-3 to Double-type Parent 90-139-14.

| PROGENY | HIGHEST NUMBER OF PETALS/FLOWER | FLOWER COLOR[1] | LEAF COLOR[2] | LEAF VARIEG-ATION[3] |
|---|---|---|---|---|
| 1 | 5 | PU, BIC | PG | S |
| 2 | 7 | PU, BIC | PG | S |
| 3 | 10 | PU, BIC | PG | S |
| 4 | 11 | PU, BIC | PG | V |
| 5 | 9 | B, BIC | G | S |
| 6 | 8 | P, BIC | PG | S |
| 7 | 7 | P, BIC | PG | S |
| 8 | 7 | O, BIC | PG | S |
| 9 | 7 | PU, BIC | PG | V |
| 10 | 7 | PU, BIC | PG | V |
| 11 | 8 | P, BIC | PG | S |
| 12 | 7 | O, BIC | PG | V |
| 13 | 7 | PU, BIC | PG | S |
| 14 | 8 | P, BIC | PG | V |
| 15 | 7 | PU, BIC | PG | S |
| 16 | 10 | P, BIC | PG | S |
| 17 | 7 | O, BIC | PG | S |
| 18 | 8 | PU, BIC | PG | S |
| 19 | 10 | PU, BIC | PG | S |
| 20 | 8 | PU, BIC | PG | S |
| 21 | 7 | PU, BIC | PG | V |
| 22 | 6 | PU, BIC | PG | S |
| 23 | 7 | PU, BIC | PG | S |
| 24 | 6 | P, BIC | PG | S |
| 25 | 6 | PU, BIC | PG | S |
| 26 | 6 | O, BIC | PG | S |
| 27 | 6 | P, BIC | PG | V |
| 28 | 5 | O, BIC | PG | S |
| 29 | 6 | P, BIC | PG | S |
| 30 | 5 | PU, BIC | PG | S |
| 31 | 5 | P, BIC | PG | S |
| 32 | 6 | P, BIC | PG | V |
| 33 | 6 | P, BIC | PG | V |
| 34 | 5 | PU, BIC | PG | S |
| 35 | 7 | P, BIC | PG | V |
| 36 | 7 | P, BIC | PG | S |
| 37 | 0 | — | — | — |
| 38 | 0 | — | — | — |

[1] B = Blush
O = Orange
P = Pink
PU = Purple
BIC = Binder

[2] G = Green
PG = Purple-Green

[3] S = Solid
V = Variegated

A single lavender single-type F1 was obtained from the cross of 90-139-14 as the female to 89-430-3 as the male. This F1 offspring was crossed, either as the male or female, in backcrosses to the double-type parent. The results of these backcrosses are shown in Table X. For each of the progeny produced from these backcrosses, the petal number of the flower with the highest number of petals was recorded. Both full and partial petals were counted. A total of 102 backcross progeny were analyzed. Of these 28 (27.5%) were single-type, 15 (14.7%) were semi-double-type, 54 (52.9%) were double-type and 5 (4.9%) failed to produce flowers.

TABLE X

Analysis of Progeny Resulting from Backcross of F1 Plants to the Double-type Parent 90-139-14: Number of Progeny in Each Petal Number Category.

| FAMILY | FEMALE | x | MALE | HIGHEST NUMBER OF PETALS/FLOWER | | | | | | | | | NO BLOOM | TOTAL PLANTS |
| --- | --- | --- | --- | --- | --- | --- | --- | --- | --- | --- | --- | --- | --- | --- |
| | | | | 5 | 6 | 7 | 8 | 9 | 10 | 11 | 12 | 13 | | |
| 91-1320 | 90-139-14 | x | 90-1221-1 | 13 | 7 | 13 | 5 | 6 | 4 | 1 | 0 | 1 | 2 | 52 |
| 90-1323 | 90-1221-1 | x | 90-139-14 | 15 | 8 | 12 | 6 | 3 | 3 | 0 | 0 | 0 | 3 | 50 |
| | TOTAL | | | 28 | 15 | 25 | 11 | 9 | 7 | 1 | 0 | 1 | 5 | 102 |
| | % TOTAL | | | 27.5 | 14.7 | 24.5 | 10.8 | 8.8 | 6.9 | 1.0 | 0 | 1.0 | 4.9 | |

The phenotypes of the progeny produced in backcross family 91-1320 are shown in Table XI. These plants resulted from the cross of 90-139-14 as the female and 90-1221-1 as the male. For each of the progeny produced from this backcross, the petal number of the flower(s) with the highest number of petals was recorded. Both full and partial petals were counted. Petal number per flower, flower color, leaf color and leaf variegation assorted independently. The progeny produced in this backcross exhibited a wide range of flower colors combined with double-type flowers, green or purple-green leaves, and foliage that was either solid or variegated.

TABLE XI

Phenotypes of Family 91-1320 Resulting from the Backcross of Double-type Parent 90-139-14 to F1 Progeny 90-1221-1.

| PROGENY | HIGHEST NUMBER OF PETALS/FLOWER | FLOWER COLOR[1] | LEAF COLOR[2] | LEAF VARIEGATION[3] |
| --- | --- | --- | --- | --- |
| 1 | 7 | P, BIC | PG | S |
| 2 | 9 | PU, BIC | G | V |
| 3 | 7 | PU, BIC | PG | S |
| 4 | 8 | PU, BIC | PG | S |
| 5 | 9 | P, BIC | G | S |
| 6 | 10 | P, BIC | PG | S |
| 7 | 8 | P, BIC | PG | S |
| 8 | 8 | O, BIC | PG | S |
| 9 | 9 | P, BIC | PG | S |
| 10 | 7 | PU, BIC | PG | S |
| 11 | 8 | B | PG | S |
| 12 | 9 | P, BIC | PG | S |
| 13 | 10 | P, BIC | G | S |
| 14 | 13 | P, BIC | PG | V |
| 15 | 7 | PU, BIC | PG | S |
| 16 | 7 | P, BIC | G | S |
| 17 | 7 | P, BIC | PG | V |
| 18 | 9 | PU, BIC | PG | S |
| 19 | 7 | PU, BIC | PG | S |
| 20 | 9 | P, BIC | PG | S |
| 21 | 10 | P, BIC | PG | S |
| 22 | 7 | PU, BIC | PG | S |
| 23 | 10 | L | G | V |
| 24 | 7 | PU, BIC | PG | S |
| 25 | 7 | PG | O, BIC | S |
| 26 | 7 | L | G | S |
| 27 | 8 | P, BIC | PG | V |
| 28 | 11 | P, BIC | PG | S |
| 29 | 7 | P, BIC | PG | V |
| 30 | 6 | PU, BIC | G | V |
| 31 | 6 | O, BIC | PG | S |
| 32 | 6 | P, BIC | G | S |
| 33 | 6 | P | G | S |
| 34 | 7 | P, BIC | PG | V |
| 35 | 5 | PU, BIC | PG | S |
| 36 | 5 | PG | P, BIC | V |
| 37 | 5 | PG | P, BIC | S |
| 38 | 5 | PU, BIC | PG | V |
| 39 | 5 | PG | PU, BIC | S |
| 40 | 6 | L | G | V |
| 41 | 5 | P, BIC | PG | V |
| 42 | 5 | PU, BIC | PG | S |
| 43 | 5 | O, BIC | PG | S |
| 44 | 5 | PU, BIC | PG | S |
| 45 | 6 | L | G | V |
| 46 | 5 | L | G | V |
| 47 | 5 | B | G | V |
| 49 | 5 | LP, SIC | PG | V |
| 49 | 5 | PU, BIC | PG | S |
| 50 | 0 | — | — | — |
| 51 | 0 | — | — | — |
| 52 | 6 | P, BIC | PG | S |

[1]B = Blush
L = Lavender
LP = Light Pink
O = Orange
P = Pink
PU = Purple
BIC = Bicolor
[2]G = Green
[3]S = Solid
V = Variegation

EXAMPLE 4

Double-flowering Cultivars Can be Produced by Backcrossing F1 Progeny to the Double-type Parent.

Controlled backcrosses to the double-type parent were conducted using the F1 progeny produced from crosses of 10 genetically distinct double-types, each having 7–10 petals per flower, with 5 genetically distinct single-types. For each of the progeny produced from these backcrosses, the petal number of the flower(s) with the highest number of petals was recorded. Among the 1,726 backcross progeny screened, 55.6% were double-type (Table XII). Two plants produced double-type flowers having 15 petals per flower. The results shown in Table XII demonstrate that the double-type characteristic can be predictably bred into diverse NGI single-type genetic backgrounds.

TABLE XII

Analysis of Progeny Produced From Backcrossing F1 Progeny to the Double-type Parent.

| HIGHEST NUMBER OF PETALS/FLOWERS | PLANTS PER PETAL NUMBER CATEGORY | % TOTAL |
| --- | --- | --- |
| 5 | 503 | 29.2 |
| 6 | 165 | 9.6 |
| 7 | 395 | 22.9 |
| 8 | 204 | 11.8 |
| 9 | 147 | 8.5 |
| 10 | 153 | 8.9 |
| 11 | 40 | 2.3 |
| 12 | 14 | .8 |
| 13 | 4 | .2 |
| 14 | 2 | |
| 15 | 2 | .1 |
| No Bloom | 97 | 5.6 |
| TOTAL PLANTS | 1,726 | |

EXAMPLE 5

Double-type NGI Cultivars Can be Produced by sibcrossing Between F1 Progeny.

Sibcrosses were conducted among F1 progeny produced from crosses of 4 genetically distinct double-types, each having 7–10 petals per flower, to 3 genetically distinct single-types. For each of the progeny produced from these sibcrosses, the petal number of the flower(s) with the highest number of petals was recorded. Both full and partial petals were counted. Among the 143 progeny screened, 35.0% were double-types. Four progeny produced 10 petals per double-type flower. The results shown in Table XIII demonstrate that the double-type characteristic can be predictably bred into diverse single-type genetic backgrounds by means of sibcrossing among the F1 progeny produced by crossing a double-type to a single-type NGI.

TABLE XIII

Summary of F1 Sibcrossing.

| HIGHEST NUMBER OF PETALS/FLOWER | PLANTS PER PETAL NUMBER CATEGORY | % TOTAL |
| --- | --- | --- |
| 5 | 72 | 50.3 |
| 6 | 14 | 9.8 |
| 7 | 28 | 19.6 |
| 8 | 6 | 4.2 |
| 9 | 12 | 8.4 |
| 10 | 4 | 2.8 |
| No Bloom | 7 | 4.9 |
| TOTAL PLANTS | 143 | |

EXAMPLE 6

Stability and Quantitative Analysis of the Double-Flowering Trait.

The stability of the double-flowering characteristic and quantitative analysis of its expression were analyzed. Crosses were made between double-flowering cultivars developed in the breeding program and double-flowering progeny were selected. Crosses were made and plants were grown as described above. In order to ascertain the stability of the double-flowering characteristic the expression of doubleness was compared among cuttings made from the selected double-flowering progeny. The double-flowering selections were grown and 5–6 cuttings were made from each selection. These cuttings were designated A through F. The cuttings were transplanted to 4 inch pots and later to 6 inch pots. The plants were allowed to bloom. The petal numbers of all flowers produced during the time of the experiment on each plant were recorded. The results are shown in Table XIV. Three different progeny (91-1303-1, 91-1303-3, and 91-1303-4) resulting from the cross of 90-132-2 to 90-1219-8 were analyzed. One selection (91-1304-15) resulting from the cross of 90-132-2 to 90-1219-9 was analyzed. Two different progeny (91-1310-5 and 91-1310-6) resulting from the cross of 90-1219-8 to 90-132-2 were analyzed. Finally, two progeny (91-1319-3 and 91-1319-6) resulting from the cross of 90-139-14 to 90-1214-3 were analyzed.

The expression of the double-type characteristic was stable among the cuttings taken from each double-type selection. There was little variation among the mean and standard deviation for petal count among the cuttings made from each of the selected double-flowering progeny.

Stable cultivars were selected which produce a wide range of petal counts among the flowers in the inflorescence. For example, 91-1310-6 produced an inflorescence containing flowers having anywhere from 6 to 17 petals per flower. Selection 91-1278-2, resulting from the backcross of 90-1202-2 to its double parent 90-109-08, produced an inflorescence containing flowers having anywhere from 8 to 26 petals per flower. Other stable cultivars were selected that produce a narrow range of petal counts among the flowers in the inflorescence. For example, 91-1319-3 produces an inflorescence containing flowers having anywhere from 7–10 petals. Cultivars 90-132-2 and 90-139-14, described above, also produce an inflorescence containing flowers having a narrow range of petals per flower.

As these data show, it is possible to select stable double-flowering cultivars wherein substantially all the flowers in the inflorescence are double-type and wherein the petal count among these flowers has either a wide or narrow range. Alternatively, it is possible to select stable double-flowering cultivars which produce an inflorescence containing single-type, semi-double-type and double-type flowers or semi-double-type and double-type flowers and wherein the petal count among these flowers has either a wide or narrow range.

TABLE XIV

Petal Number Analysis

| Cultivar | Parents | Low Petal Number Per Flower | High Petal Number Per Flower | Mean | Standard Deviation |
|---|---|---|---|---|---|
| 91-1303-1 | 90-132-2 X 90-1219-8 | | | | |
| A | | 5 | 9 | 5.7 | 1.3 |
| B | | 5 | 10 | 5.7 | 1.3 |
| C | | 5 | 9 | 5.4 | 1.2 |
| D | | 5 | 9 | 5.6 | 1.0 |
| E | | 5 | 7 | 5.3 | 0.6 |
| F | | 5 | 9 | 5.5 | 1.1 |
| All Data | | 5 | 10 | 5.6 | 1.2 |
| 91-1303-3 | 90-132-2 X 90-1219-8 | | | | |
| A | | 5 | 11 | 7.9 | 1.9 |
| B | | 7 | 12 | 9.2 | 1.6 |
| C | | 5 | 10 | 8.1 | 1.7 |
| D | | 5 | 12 | 8.5 | 1.7 |
| E | | 5 | 11 | 7.6 | 2.0 |
| F | | 6 | 10 | 7.2 | 1.5 |
| All Data | | 5 | 12 | 8.0 | 1.8 |
| | | 49 | | | |
| 9-1303-4 | 90-132-2 X 90-1219-8 | | | | |
| A | | 7 | 11 | 9.3 | 1.0 |
| B | | 8 | 12 | 10.0 | 1.4 |
| C | | 8 | 10 | 9.4 | 0.7 |
| D | | 8 | 10 | 9.0 | 1.0 |
| E | | 8 | 11 | 9.3 | 1.0 |
| All Data | | 7 | 12 | 9.4 | 1.0 |
| 91-1304-15 | 90-132-2 X 90-1219-9 | | | | |
| A | | 5 | 10 | 6.5 | 1.8 |
| B | | 5 | 9 | 6.9 | 1.4 |
| C | | 5 | 10 | 7.4 | 1.9 |
| D | | 5 | 11 | 7.3 | 2.0 |
| E | | 5 | 13 | 8.1 | 2.2 |
| F | | 5 | 10 | 6.9 | 1.5 |
| All Data | | 5 | 13 | 7.2 | 1.9 |
| 91-1310-5 | 90-1219-8 X 90-132-2 | | | | |
| A | | 6 | 12 | 9.1 | 1.2 |
| B | | 7 | 12 | 9.4 | 1.3 |
| C | | 7 | 11 | 9.0 | 1.3 |
| D | | 7 | 10 | 8.3 | 0.9 |
| E | | 9 | 15 | 9.8 | 1.3 |
| F | | 8 | 11 | 9.7 | 1.0 |
| All Data | | 6 | 15 | 9.2 | 1.2 |
| F | | 8 | 11 | 9.7 | 1.0 |
| All Data | | 6 | 15 | 9.2 | 1.2 |
| 91-1310-6 | 90-1219-9 X 90-132-2 | | | | |
| A | | 7 | 12 | 8.8 | 1.4 |
| B | | 7 | 11 | 9.2 | 1.1 |
| C | | 7 | 17 | 9.0 | 2.5 |
| D | | 6 | 10 | 8.3 | 1.3 |
| E | | 6 | 13 | 8.8 | 1.5 |
| F | | 7 | 12 | 8.8 | 1.4 |
| All Data | | 6 | 17 | 8.8 | 1.8 |
| 91-1319-3 | 90-139-14 X 90-1214-3 | | | | |
| A | | 7 | 9 | 8.0 | 1.0 |
| B | | 9 | 10 | 9.5 | 0.7 |
| C | | 8 | 8 | 8.0 | 0.0 |
| D | | 8 | 8 | 8.0 | 0.0 |
| E | | 8 | 9 | 8.5 | 0.6 |
| F | | 8 | 10 | 8.6 | 0.9 |
| All Data | | 7 | 10 | 8.5 | 0.8 |
| 91-1319-6 | 90-139-14 X 90-1214-3 | | | | |
| A | | 7 | 9 | 8 | 0.6 |
| B | | 7 | 8 | 7.8 | 0.5 |
| C | | 7 | 8 | 7.8 | 0.5 |
| D | | 7 | 8 | 7.3 | 0.5 |
| E | | 7 | 8 | 7.8 | 0.5 |
| F | | 6 | 8 | 7.4 | 0.8 |
| All Data | | 6 | 9 | 7.6 | 0.7 |

The double-type characteristic can be predictably bred into diverse single-type or semi-double-type NGI genetic backgrounds using the methods described hereinabove. Double-flowering NGI cultivars can be predictably selected in which substantially all the flowers produced are double-type. The degree of doubleness per flower or plant can be predictably increased by means of recurrent selection. The double-type characteristic can be predictably combined with other desirable NGI characteristics to produce commercially acceptable cultivars that can be stably reproduced by asexual propagation.

The invention has been described with reference to various specific and preferred embodiments and techniques. However, it should be understood that many variations and modifications may be made while remaining within the spirit and scope of the invention. The relevant portions of the references cited herein are incorporated by reference.

What is claimed is:

1. A New Guinea Impatiens plant, produced by conventional breeding methods, which has one or more double-type flowers with at least 7 full or partial petals per flower.

2. The New Guinea Impatiens plant according to claim 1 wherein substantially all the flowers produced by said plant are double-type having at least 7 full or partial petals per flower.

3. A method for the breeding of double-flowering New Guinea Impatiens plants that produce one or more flowers with at least 7 full or partial petals per flower comprising the steps of:
   a. crossing a first single-type plant having doubleness in its genetic background, either as the male or female parent to:
      i. a semi-double-type plant;
      ii. a double-type plant; or
      iii. a second single-type plant having doubleness in its genetic background;
   b. selecting F1 progeny that are single-type, semi-double-type or double-type;
   c. crossing said F1 progeny that are single-type, semi-double-type or double-type to:
      i. a second double-type plant;
      ii. a second semi-double-type plant; or
      iii. a third single-type plant having doubleness in its genetic background; and
   d. selecting double-flowering progeny.

4. The method according to claim 3, wherein said first, second and third single-type plants, or first and second semi-double-type or double-type plants are the same or different cultivars.

5. A method for the breeding of double-flowering New Guinea Impatiens plants that produce one or more flowers with at least 7 full or partial petals per flower comprising the steps of:
   a. crossing a first semi-double-type plant, either as the male or female parent to:
      i. a second semi-double-type plant;
      ii. a double-type plant;
      iii. a single-type plant having doubleness in its genetic background;
   b. selecting F1 progeny that are single-type, semi-double-type or double-type;
   c. crossing said F1 progeny that are single-type, semi-double-type or double-type to:
      i. a second double-type plant;
      ii. a third semi-double-type plant;
      iii. a second single-type plant having doubleness in its genetic background; or
      iv. a second single-type plant with no known doubleness in its genetic background; and
   d. selecting double-flowering progeny.

6. The method according to claim 5, wherein said first and second single-type and double-type plants, or first, second and third semi-double-type plants are some or different cultivars.

7. A method for the breeding of double-flowering New Guinea Impatiens plants that produce one or more flowers with at least 7 full or partial petals per flower comprising the steps of:
   a. crossing a first double-type plant, either as the male or female parent to:
      i. a semi-double-type plant;
      ii. a second double-type plant;
      iii. a single-type plant having doubleness in its genetic background; or
      iv. a single-type plant with no known doubleness in its genetic background;
   b. selecting F1 progeny that are single-type, semi-double-type or double-type;
   c. crossing said F1 progeny that are single-type, semi-double-type or double-type to:
      i. a third double-type plant;
      ii. a second semi-double-type plant;
      iii. a second single-type plant having doubleness in its genetic background; or
      iv. a second single-type plant with no known doubleness in its genetic background; and
   d. selecting double-flowering progeny.

8. The method according to claim 7, wherein said first, second and third double-type plants, or first and second single-type or semi-double-type plants are the same or different cultivars.

* * * * *

UNITED STATES PATENT AND TRADEMARK OFFICE
CERTIFICATE OF CORRECTION

PATENT NO. : 5,684,225
DATED : November 4, 1997
INVENTOR(S) : Lyndon DREWLOW et al.

It is certified that error appears in the above-identified patent and that said Letters Patent is hereby corrected as shown below:

On the title page,

Item [*] Notice, "Pat. No. Plant 8,018" should read --Pat. No. Plant 8,907--.

Signed and Sealed this

Eleventh Day of May, 1999

Attest:

Q. TODD DICKINSON

*Attesting Officer*     *Acting Commissioner of Patents and Trademarks*